United States Patent
Fuchiwaki et al.

(10) Patent No.: US 10,084,142 B2
(45) Date of Patent: Sep. 25, 2018

(54) CARBAZOLE COMPOUND, MATERIAL FOR ORGANIC ELECTROLUMINESCENT DEVICE, AND ORGANIC ELECTROLUMINESCENT DEVICE

(71) Applicant: SAMSUNG DISPLAY CO., LTD., Yongin-si, Gyeonggi-do (KR)

(72) Inventors: Junta Fuchiwaki, Yokohama (JP); Hiroaki Itoi, Yokohama (JP)

(73) Assignee: Samsung Display Co., Ltd., Yongin-si (KR)

( * ) Notice: Subject to any disclaimer, the term of this patent is extended or adjusted under 35 U.S.C. 154(b) by 175 days.

(21) Appl. No.: 14/967,207

(22) Filed: Dec. 11, 2015

(65) Prior Publication Data

US 2016/0172597 A1    Jun. 16, 2016

(30) Foreign Application Priority Data

Dec. 15, 2014 (JP) ................ 2014-252995

(51) Int. Cl.
| | |
|---|---|
| *H01L 51/50* | (2006.01) |
| *H01L 51/00* | (2006.01) |
| *C07D 209/86* | (2006.01) |

(52) U.S. Cl.
CPC ........ *H01L 51/0072* (2013.01); *C07D 209/86* (2013.01); *H01L 51/006* (2013.01);
(Continued)

(58) Field of Classification Search
CPC ............. H01L 51/0072; H01L 51/0052; H01L 51/0059; H01L 51/006; H01L 51/5056; C07D 209/86
(Continued)

(56) References Cited

U.S. PATENT DOCUMENTS

| 8,394,510 B2 | 3/2013 | Mizuki et al. |
| 2010/0244008 A1 | 9/2010 | Lee et al. |

(Continued)

FOREIGN PATENT DOCUMENTS

| JP | 2011-503056 A | 1/2011 |
| JP | 2014-101275 A | 6/2014 |

(Continued)

OTHER PUBLICATIONS

Abstract for International Pub. No. WO 2009061156 A1, dated May 14, 2009, for corresponding JP 2011-503056 A, 2 pages.

*Primary Examiner* — Jayne L Mershon
(74) *Attorney, Agent, or Firm* — Lewis Roca Rothgerber Christie LLP

(57) ABSTRACT

An organic electroluminescent device includes: a substrate; a first electrode on the substrate; a second electrode on the first electrode; and a plurality of lamination layers between the first and second electrodes; wherein at least one of the plurality of lamination layers includes a carbazole compound represented by Formula 1:

(Continued)

Formula 1

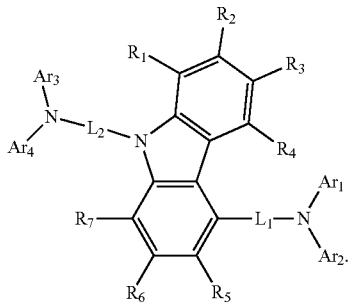

The carbazole compound may improve the emission efficiency of the organic electroluminescent device.

20 Claims, 1 Drawing Sheet

(52) U.S. Cl.
CPC ...... *H01L 51/0052* (2013.01); *H01L 51/0059* (2013.01); *H01L 51/5056* (2013.01)

(58) Field of Classification Search
USPC .......................................................... 428/690
See application file for complete search history.

(56) References Cited

U.S. PATENT DOCUMENTS

2014/0217392 A1   8/2014  Hong et al.
2014/0296519 A1*  10/2014 Matsumoto .......... C07D 209/86
                                               544/212

FOREIGN PATENT DOCUMENTS

| JP | 2014-532303 A | 12/2014 |
| WO | WO 2005/090512 A1 | 9/2005 |
| WO | WO 2009/061156 A1 | 5/2009 |
| WO | WO 2010/095621 A1 | 8/2010 |
| WO | WO 2011/024451 A1 | 3/2011 |
| WO | WO 2011/102112 A1 | 8/2011 |
| WO | WO 2013/183851 A1 | 12/2013 |
| WO | WO 2014/021569 A1 | 2/2014 |

* cited by examiner

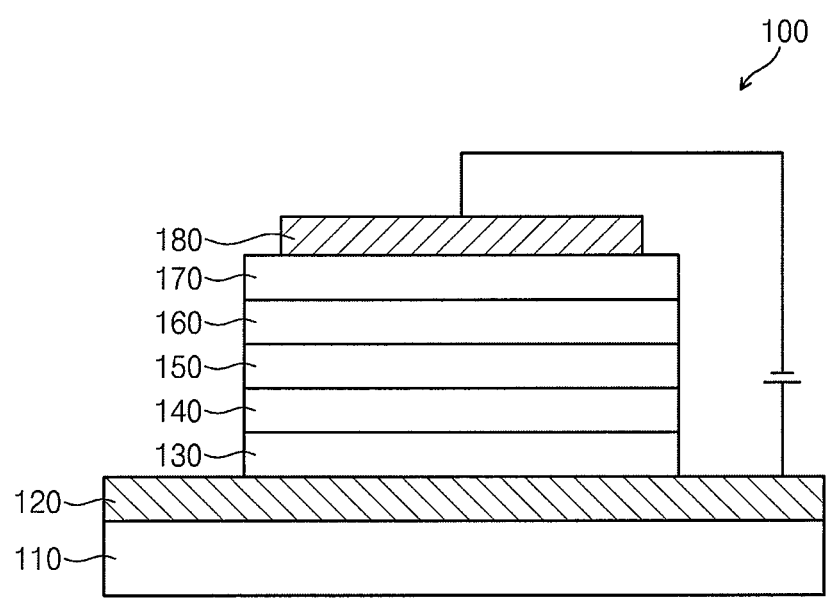

CARBAZOLE COMPOUND, MATERIAL FOR ORGANIC ELECTROLUMINESCENT DEVICE, AND ORGANIC ELECTROLUMINESCENT DEVICE

CROSS-REFERENCE TO RELATED APPLICATION

This patent application claims priority to and the benefit of Japanese Patent Application No. 2014-252995, filed on Dec. 15, 2014, the entire content of which is hereby incorporated by reference.

BACKGROUND

One or more aspects of embodiments of the present disclosure herein are directed toward a carbazole compound, a material for use in an organic electroluminescent device, and an organic electroluminescent device.

Recently, organic electroluminescent (EL) displays have been actively developed. In addition, organic electroluminescent devices, which are self-emitting devices used in organic electroluminescent displays, have also been actively developed.

An example structure of an organic electroluminescent device includes an anode, a hole injection layer, a hole transport layer, an emission layer, an electron transport layer, an electron injection layer, and a cathode that are successively laminated (e.g., in the stated order). In such organic electroluminescent device, holes and electrons, respectively injected from an anode and cathode, are recombined in the emission layer to generate excitons, and afterwards, light is emitted when the generated excitons are transited to the ground state.

To improve the performance of organic electroluminescent devices, various compounds are being investigated as a material to be used in each lamination layer (e.g., in each of the layers included in the example structure of an organic electroluminescent device described above). For example, a carbazole compound which may be used as a hole transport material in an organic electroluminescent device has been previously described.

However, an organic electroluminescent device which uses the previously described carbazole compound may exhibit insufficient emission efficiency.

SUMMARY

One or more aspects of embodiments of the present disclosure are directed toward a novel and improved carbazole compound which may improve the emission efficiency of an organic electroluminescent device, a material including the carbazole compound and for use in the organic electroluminescent device, and the organic electroluminescent device which includes the carbazole compound.

An embodiment of the present inventive concept provides a carbazole compound represented by the following Formula 1:

Formula 1

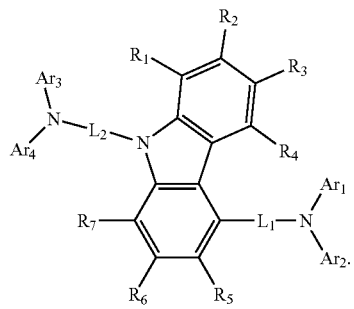

In Formula 1, $R_1$ to $R_7$ may be each independently selected from hydrogen, a halogen atom, a hydroxyl group, a cyano group, a nitro group, an alkoxy group, an aryloxy group, an alkyl or aryl substituted silyl group, a substituted or unsubstituted alkyl group, a substituted or unsubstituted aryl group, and a substituted or unsubstituted heteroaryl group; $Ar_1$ to $Ar_4$ may be each independently selected from a substituted or unsubstituted alkyl group, a substituted or unsubstituted aryl group, and a substituted or unsubstituted heteroaryl group; and $L_1$ and $L_2$ may be each independently selected from a single bond and a substituted or unsubstituted arylene group.

Accordingly, the emission efficiency of an organic electroluminescent device which includes such carbazole compound may be improved.

In an embodiment, at least one selected from $L_1$ and $L_2$ may be a single bond or a substituted or unsubstituted connecting group selected from the following groups collectively denoted as Formula 2:

Formula 2

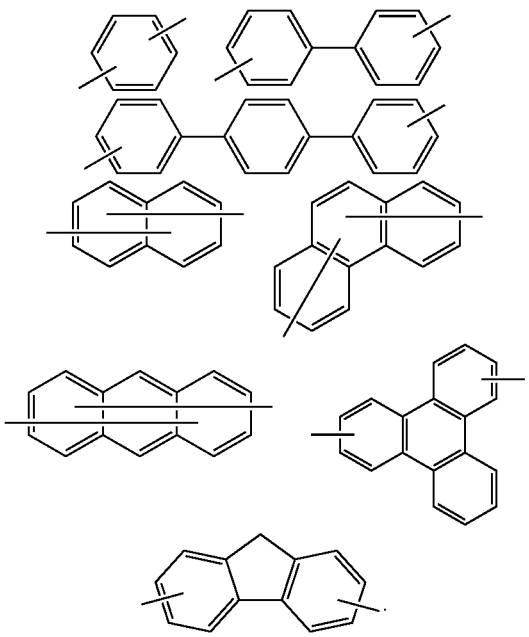

Accordingly, the emission efficiency of an organic electroluminescent device which includes such carbazole compound may be further improved.

In an embodiment, at least one selected from $L_1$ and $L_2$ may be a single bond or a substituted or unsubstituted connecting group selected from the following groups collectively denoted as Formula 3:

Formula 3

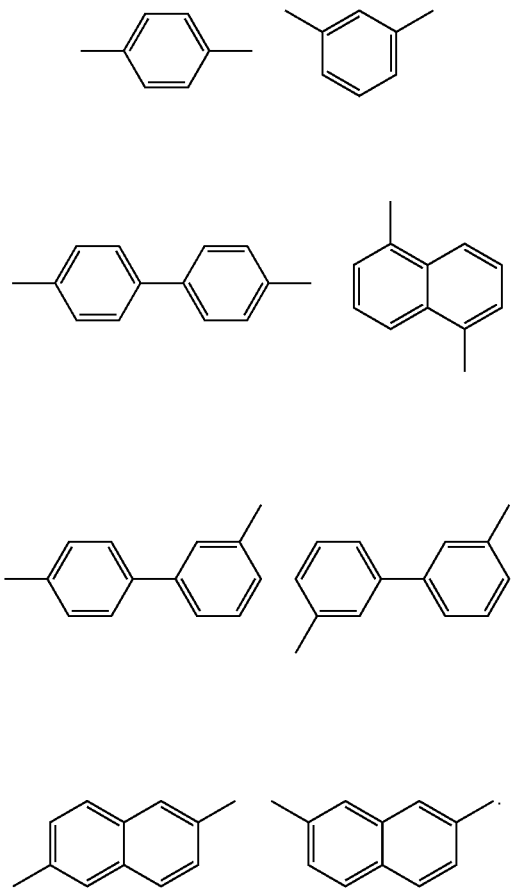

Accordingly, the emission efficiency of an organic electroluminescent device which includes such carbazole compound may be further improved.

In an embodiment, at least one selected from $L_1$ and $L_2$ may be a substituted or unsubstituted connecting group selected from the following groups collectively denoted as Formula 4:

Formula 4

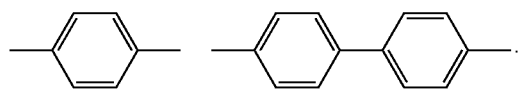

Accordingly, the emission efficiency of an organic electroluminescent device which includes such carbazole compound may be further improved.

In an embodiment, $Ar_1$ to $Ar_4$ may be each independently a substituted or unsubstituted aryl group or a substituted or unsubstituted heteroaryl group selected from the following groups collectively denoted as Formula 5:

Formula 5

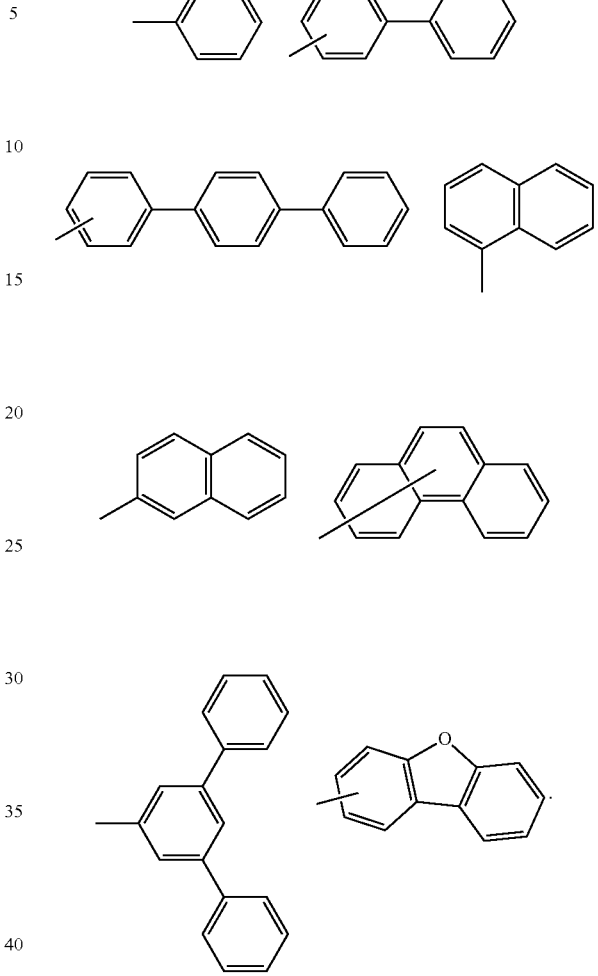

Accordingly, the emission efficiency of an organic electroluminescent device which includes such carbazole compound may be further improved.

In an embodiment, $Ar_1$ to $Ar_4$ may comprise up to 14 carbon atoms for forming a ring.

Accordingly, the emission efficiency of an organic electroluminescent device which includes such carbazole compound may be further improved.

In an embodiment, $R_1$ to $R_7$ may be each independently selected from hydrogen, a fluorine atom, a cyano group, a methyl group, and a phenyl group.

Accordingly, the emission efficiency of an organic electroluminescent device which includes such carbazole compound may be further improved.

In an embodiment, the carbazole compound may have a molecular weight of 500 to 1000.

Accordingly, the emission efficiency of an organic electroluminescent device which includes such carbazole compound may be further improved.

In an embodiment, the carbazole compound may be selected from Compounds 1, 2, 9, and 11 to 13.

1

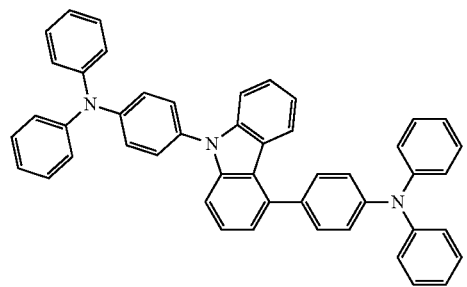

2

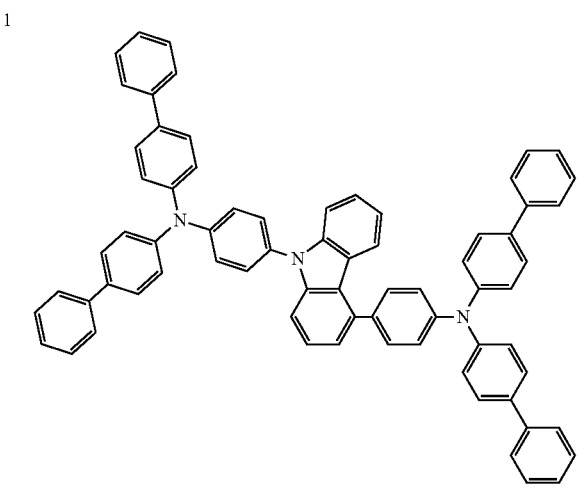

9

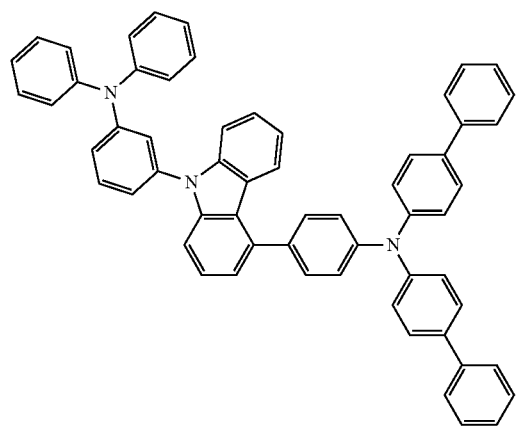

11

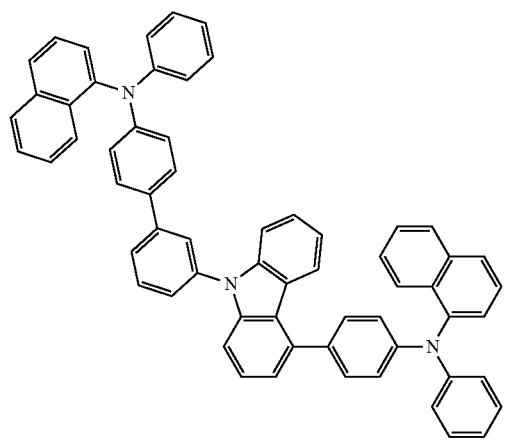

12

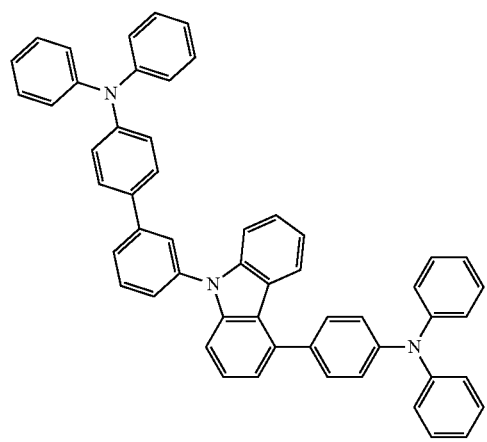

13

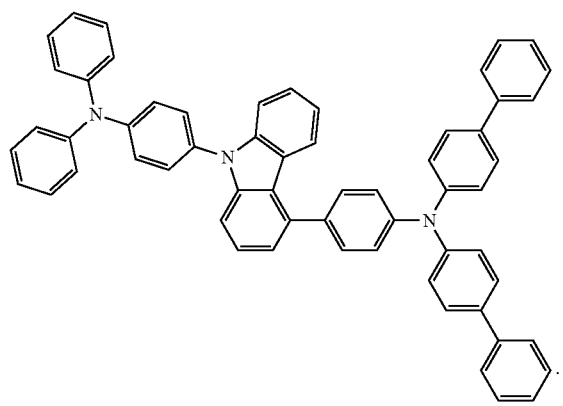

Accordingly, the emission efficiency of an organic electroluminescent device which includes such carbazole compound may be further improved.

Another embodiment of the inventive concept provides a material for use in an organic electroluminescent device, the material including the carbazole compound.

Accordingly, the emission efficiency of an organic electroluminescent device which includes such material for use in the organic electroluminescent device may be improved.

Another embodiment of the inventive concept provides an organic electroluminescent device, including a substrate; a first electrode on the substrate; a second electrode on the first electrode; and a plurality of lamination layers between the first and second electrodes; wherein at least one of the plurality of lamination layers includes a carbazole compound represented by the following Formula 1:

Formula 1

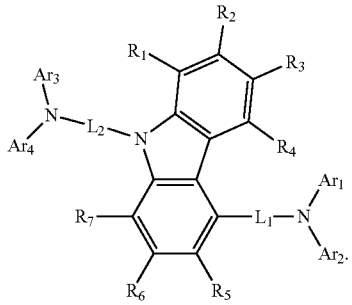

In Formula 1, $R_1$ to $R_7$ may be each independently selected from hydrogen, a halogen atom, a hydroxyl group, a cyano group, a nitro group, an alkoxy group, an aryloxy group, an alkyl or aryl substituted silyl group, a substituted or unsubstituted alkyl group, a substituted or unsubstituted aryl group, and a substituted or unsubstituted heteroaryl group; $Ar_1$ to $Ar_4$ may be each independently selected from a substituted or unsubstituted alkyl group, a substituted or unsubstituted aryl group, and a substituted or unsubstituted heteroaryl group; and $L_1$ and $L_2$ may be each independently selected from a single bond and a substituted or unsubstituted arylene group.

In an embodiment, the plurality of lamination layers may include a hole transport layer which includes the carbazole compound represented by the above Formula 1.

Accordingly, an organic electroluminescent device having improved emission efficiency may be provided.

BRIEF DESCRIPTION OF THE FIGURES

The accompanying drawing is included to provide a further understanding of the inventive concept, and is incorporated in and constitutes a part of this specification. The drawing illustrates example embodiments of the present inventive concept and, together with the description, serves to explain principles of the present inventive concept. The drawing is a schematic diagram illustrating one example of an organic electroluminescent device according to an embodiment of the present inventive concept.

DETAILED DESCRIPTION

Hereinafter, example embodiments of the present inventive concept will be described with reference to the accompanying drawing. Moreover, in the description and drawing, like reference numerals refer to like elements or elements having like functions throughout, and duplicative explanations thereof will not be provided herein.

1. CARBAZOLE COMPOUND ACCORDING TO AN EMBODIMENT OF THE PRESENT INVENTIVE CONCEPT

Hereinafter, a description of a carbazole compound according to an embodiment of the inventive concept will be provided. A carbazole compound according to the present embodiment may be represented by the following Formula 1:

Formula 1

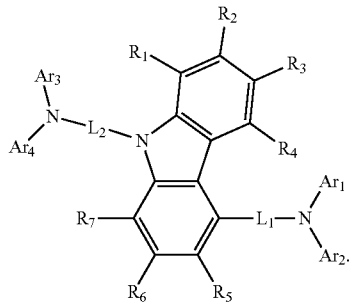

In the above Formula 1, $R_1$ to $R_7$ may be each independently selected from hydrogen, a halogen atom, a hydroxyl group, a cyano group, a nitro group, an alkoxy group, an aryloxy group, an alkyl or aryl substituted silyl group, a substituted or unsubstituted alkyl group, a substituted or unsubstituted aryl group, and a substituted or unsubstituted heteroaryl group; $Ar_1$ to $Ar_4$ may be each independently selected from a substituted or unsubstituted alkyl group, a substituted or unsubstituted aryl group, and a substituted or unsubstituted heteroaryl group; and $L_1$ and $L_2$ may be each independently selected from a single bond and a substituted or unsubstituted arylene group.

In the carbazole compound according to the present embodiment, as shown in the Formula 1, arylamino groups are coupled to a carbazole ring, directly (e.g., via a bond such as a single bond) or through a linker (e.g., a connecting group), at positions 4 and 9 of the carbazole ring. Such carbazole compound may be suitable for use as a hole transport material in an organic electroluminescent device.

For example, in the carbazole compound according to the present embodiment, since arylamino groups are coupled at positions 4 and 9 of the carbazole ring, the band gaps of a highest occupied molecular orbital (HOMO) and a lowest unoccupied molecular orbital (LUMO) are increased. Accordingly, the carbazole compound of the present embodiment improves the hole transporting ability and may function to prevent or reduce an influx of electrons from an emission layer into a hole transport layer (e.g., may exhibit electron blocking ability), and thus the emission efficiency of the organic electroluminescent device including the carbazole compound may be improved.

For example, in the carbazole compound according to the present embodiment, when an arylamino group is coupled at position 9 of the carbazole ring, electron repulsion between the lone pairs of electrons of nitrogen atoms (e.g., the nitrogen atom included in the amine group and the nitrogen atom included in the carbazole ring) causes a decrease in the energy level of the LUMO (e.g., the absolute value of the energy level is low). This improves the electron blocking ability, and thus the carbazole compound according to the present embodiment may reduce the influx of electrons from the emission layer into the hole transport layer and reduce the ineffective current which does not contribute to emission.

Moreover, in the carbazole compound according to the present embodiment, when an arylamino group is substituted at position 4 of the carbazole ring, steric hindrance causes a torsion angle between the carbazole ring and the arylamino group to be increased. Accordingly, since the band gap between HOMO and LUMO is increased, the carbazole compound according to the present embodiment may effectively block or reduce the excimers generated in the emission layer from flowing into the hole transport layer, and may improve the emission efficiency.

The carbazole compound according to the present embodiment has desirable properties as a hole transport material, and may thus be included in at least one of the layers disposed (e.g., positioned) between the emission layer and an anode in an organic electroluminescent device. For example, the carbazole compound according to the present embodiment may be included in the hole transport layer in an organic electroluminescent device.

For example, the carbazole compound according to the present embodiment may be suitable for use in a blue light-emitting organic electroluminescent device which requires a high hole transporting ability and electron blocking ability.

To effectively realize the electron blocking ability, the carbazole compound according to the present embodiment may be included in a layer which is disposed (e.g., positioned) in the vicinity of the emission layer, and in some embodiments, may be included in a layer which is adjacent to the emission layer.

However, in an organic electroluminescent device of embodiments of the present disclosure, layers which include the carbazole compound are not limited to the examples given above. For example, the carbazole compound according to the present embodiment may be included in any one of the layers disposed between the anode and cathode in an organic electroluminescent device.

At least one selected from $L_1$ and $L_2$ in the above Formula 1 may be a single bond or any one of substituted or unsubstituted connecting groups represented by the following structural formulae and collectively denoted as Formula 2 (e.g., at least one selected from $L_1$ and $L_2$ may be a single bond or a substituted or unsubstituted connecting group selected from the following groups collectively denoted as Formula 2). For example, at least one selected from $L_1$ and $L_2$ may be a single bond, any one of unsubstituted connecting groups represented by the following structural formulae (Formula 2), or any one of substituted connecting groups represented by the structural following formulae (Formula 2) and substituted by any suitable substituent.

Formula 2

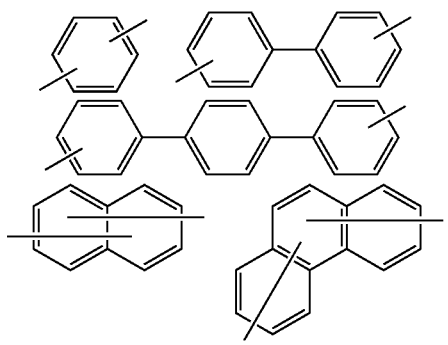

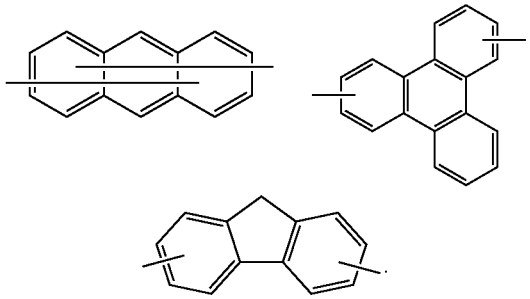

In some embodiments, at least one selected from $L_1$ and $L_2$ may be a single bond or any one of substituted or unsubstituted connecting groups represented by the following structural formulae and collectively denoted as Formula 3 (e.g., at least one selected from $L_1$ and $L_2$ may be a single bond or a substituted or unsubstituted connecting group selected from the following groups collectively denoted as Formula 3). For example, at least one selected from $L_1$ and $L_2$ may be a single bond, any one of unsubstituted connecting groups represented by the structural formulae (Formula 3), or any one of substituted connecting groups represented by the structural formulae (Formula 3) and substituted by any suitable substituent.

Formula 3

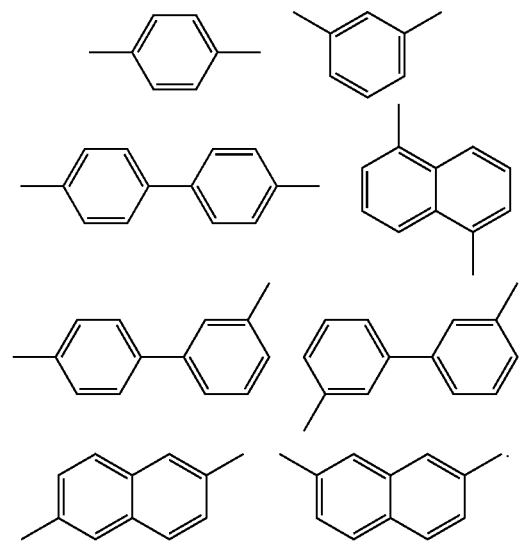

In some embodiments, at least one selected from $L_1$ and $L_2$ may be a single bond or a connecting group in which a bonding position of a carbazole ring and a bonding position of an arylamino group are para-coordinated (e.g., a carbazole ring and an arylamino group may be coupled to the connecting group at para positions). In some embodiments, at least one selected from $L_1$ and $L_2$ may be any one of substituted or unsubstituted connecting groups represented by the following structural formulae and collectively denoted as Formula 4 (e.g., at least one selected from $L_1$ and $L_2$ may be a substituted or unsubstituted connecting group selected from the following groups collectively denoted as Formula 4). For example, at least one selected from $L_1$ and $L_2$ may be any one of unsubstituted connecting groups represented by the following structural formulae (Formula 4), or any one of substituted connecting groups represented by the structural formulae (Formula 4) and substituted by any suitable substituent.

Formula 4

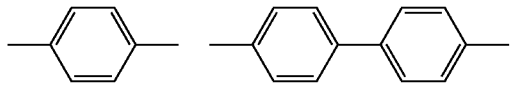

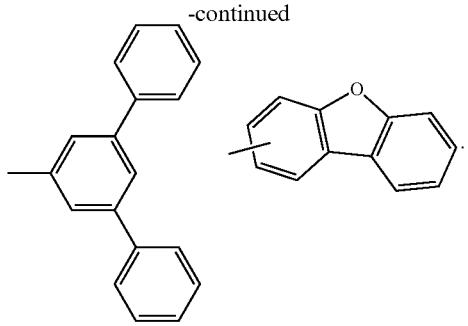
-continued

When at least one selected from $L_1$ and $L_2$ is a connecting group or a single bond, as described above, the torsion angle between the carbazole ring and the arylamino group is further increased in the carbazole compound according to the present embodiment. Accordingly, the band gap between the HOMO and LUMO is increased even further, and thus the carbazole compound according to the present embodiment may improve the hole transporting ability and electron blocking ability even further.

In Formula 1, the $Ar_1$ to $Ar_4$ may be each independently selected from substituted or unsubstituted aryl groups and substituted or unsubstituted heteroaryl groups represented by the following structural formulae and collectively denoted as Formula 5 (e.g., $Ar_1$ to $Ar_4$ may be each independently a substituted or unsubstituted aryl group or a substituted or unsubstituted heteroaryl group selected from the following groups collectively denoted as Formula 5). For example, the $Ar_1$ to $Ar_4$ may be each independently selected from unsubstituted aryl and heteroaryl groups represented by the following structural formulae (Formula 5), and substituted aryl and heteroaryl groups represented by the following structural formulae (Formula 5) and substituted by any suitable substituent.

Formula 5

When the $Ar_1$ to $Ar_4$ are as described above, the hole transporting ability of the carbazole compound according to an embodiment of the present disclosure may be further improved so that the emission efficiency of an organic electroluminescent device including the carbazole compound may also be further improved.

In some embodiments, the $Ar_1$ to $Ar_4$ may be an aryl or heteroaryl group having up to 14 carbon atoms for forming a ring. For example, the $Ar_1$ to $Ar_4$ may be each independently selected from a phenyl group, a biphenyl group, and a naphthyl group. As used herein, an expression "atoms for forming a ring" may refer to "ring-forming atoms."

When the molecular weight of a carbazole compound is excessively large, the film formability in the deposition process may be degraded. Thus, in embodiments of the present disclosure, the $Ar_1$ to $Ar_4$ may be a substituent having a small molecular weight, for example, an aryl or heteroaryl group having up to 14 carbon atoms for forming a ring. Here, although the minimum number of carbon atoms for forming a ring in the $Ar_1$ to $Ar_4$ is not specifically limited, number of carbon atoms may be at least 6 in the aryl group and at least 1 in the heteroaryl group.

The carbazole compound of embodiments of the present disclosure may have a molecular weight of about 500 to about 1,000. When the molecular weight of the carbazole compound exceeds about 1,000, the film formability during the deposition process may be degraded. When the molecular weight of the carbazole compound is less than about 500, the heat resistance may be degraded.

The $R_1$ to $R_7$ in Formula 1 may be each independently selected from hydrogen, a halogen atom, a hydroxyl group, a cyano group, a nitro group, an alkoxy group, an aryloxy group, an alkyl or aryl substituted silyl group, a substituted or unsubstituted alkyl group, a substituted or unsubstituted aryl group, a substituted or unsubstituted heteroaryl group, etc., or any substituents thereof. In some embodiments, the $R_1$ to $R_7$ may be each independently selected from hydrogen, a fluorine atom, a cyano group, a methyl group, and a phenyl group.

The carbazole compound according to the present embodiments may be selected from Compounds 1 to 28. For example, any of Compounds 1, 2, 9, and 11 to 13 may be used as a hole transfer material. However, the carbazole compound according to the present embodiment is not limited to the following compounds.

1
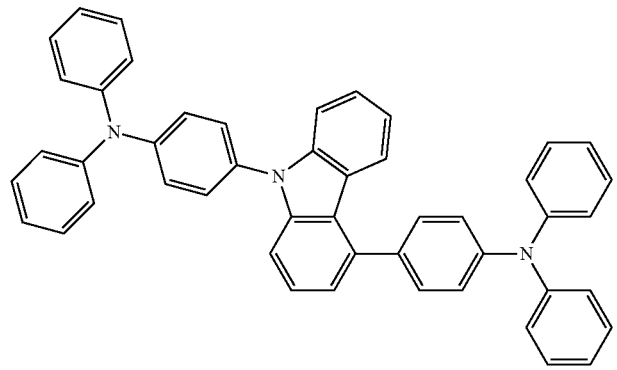
2
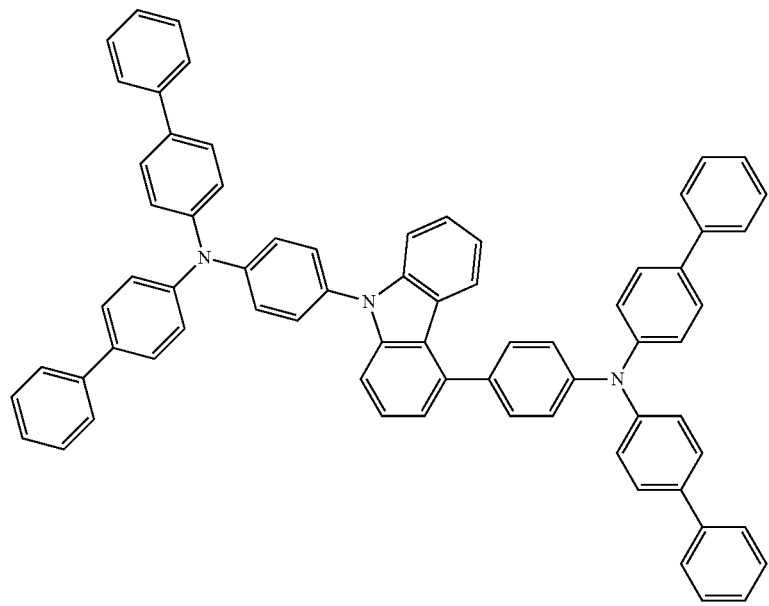
3
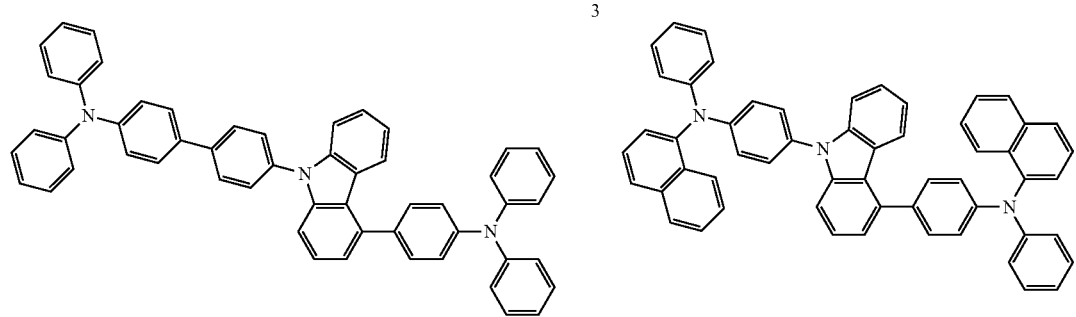
4
5
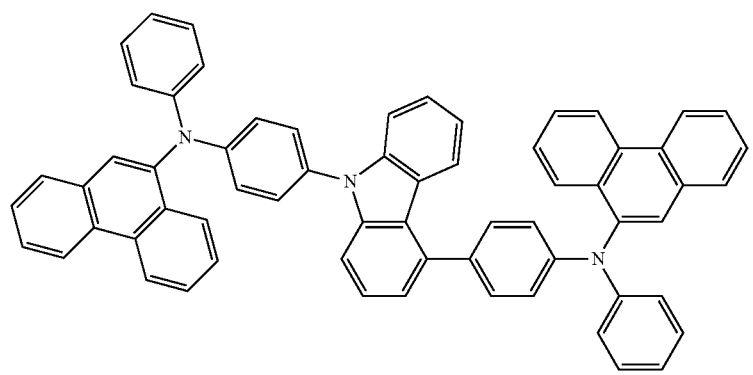

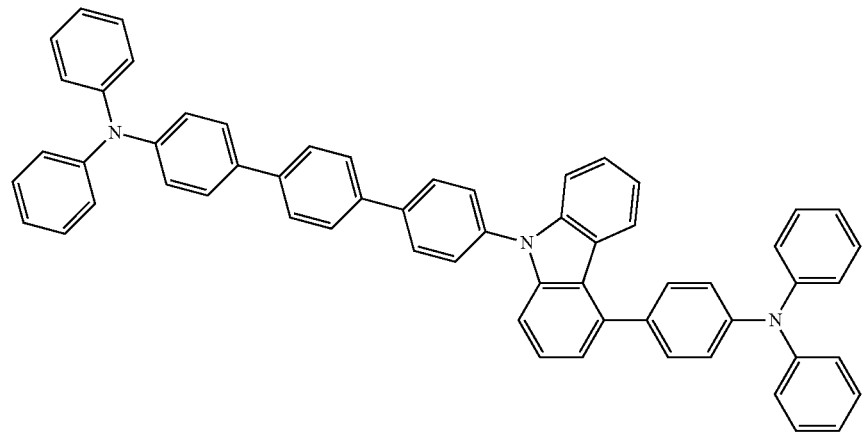
6
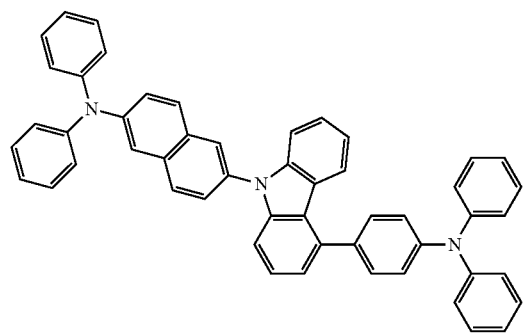
7
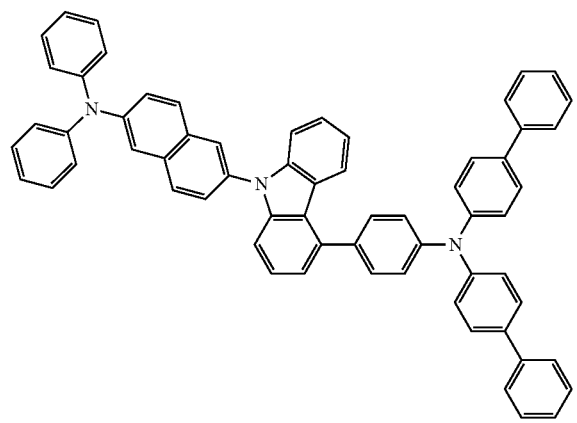
8
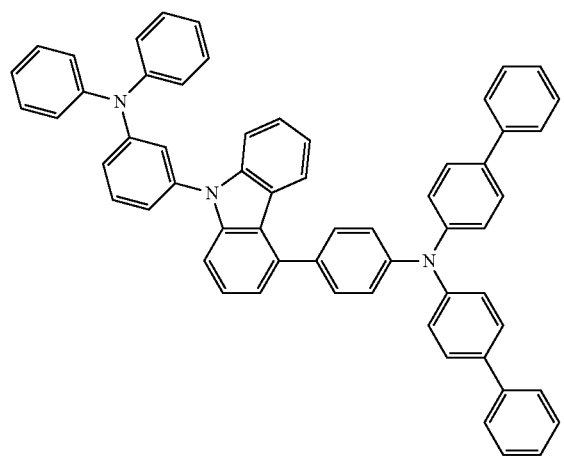
9
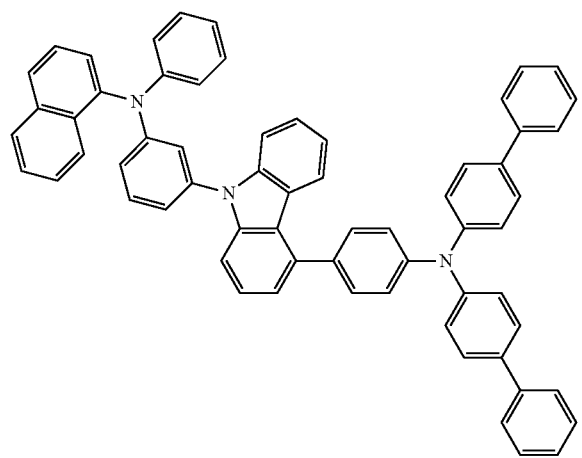
10

-continued
11
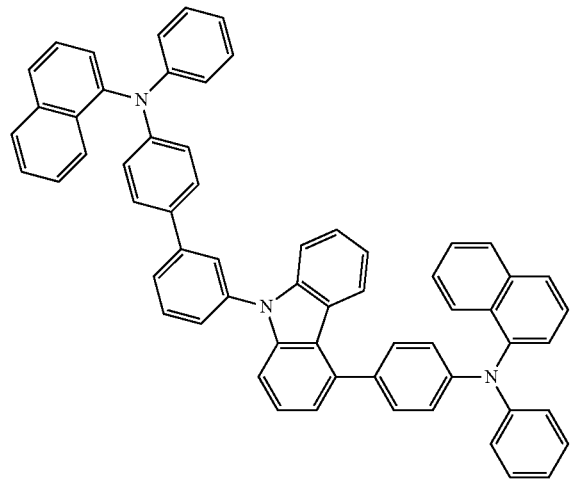
12
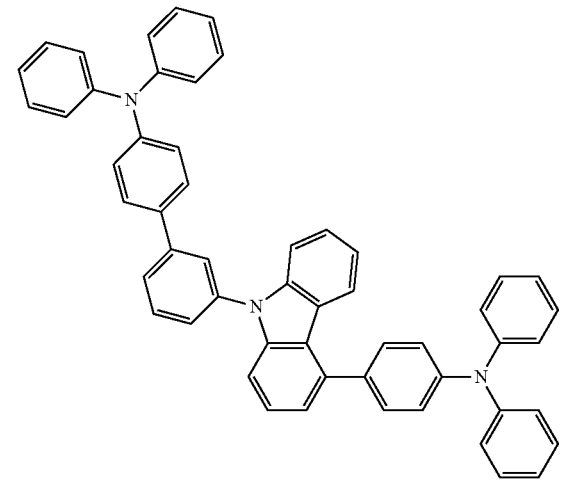
13
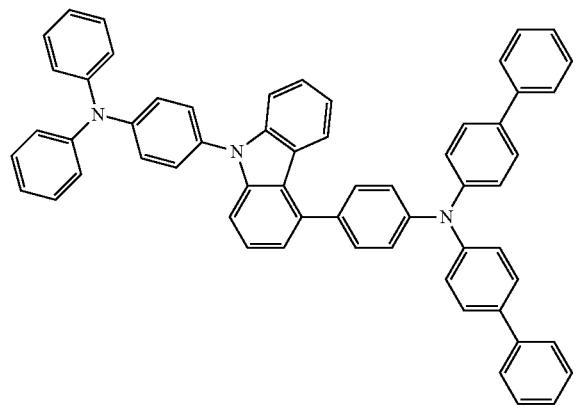
14
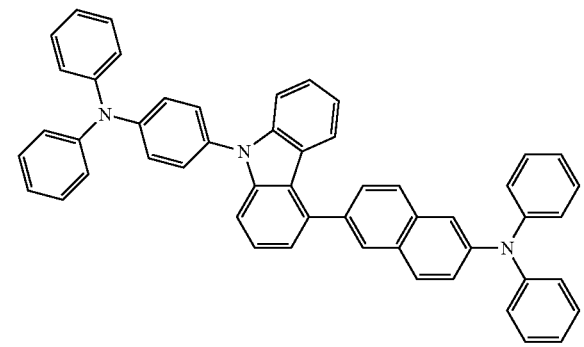
15
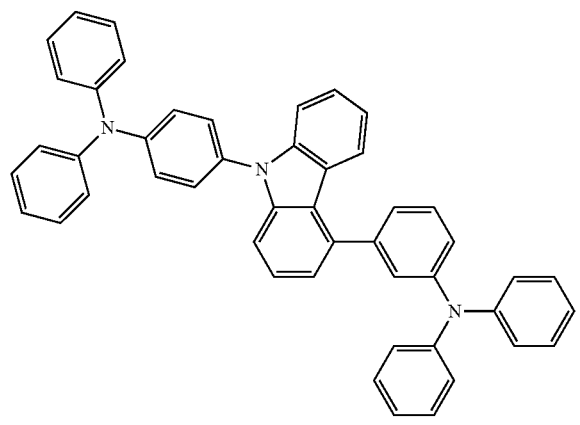
16
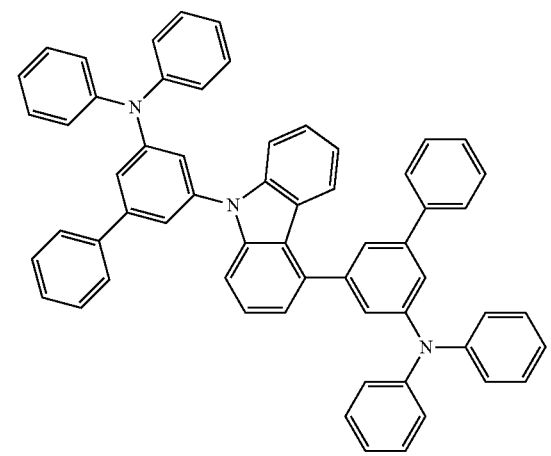

-continued
17
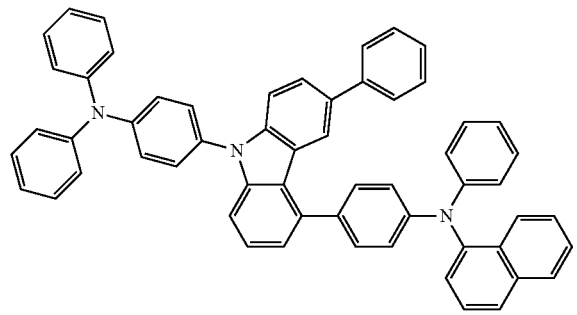
18
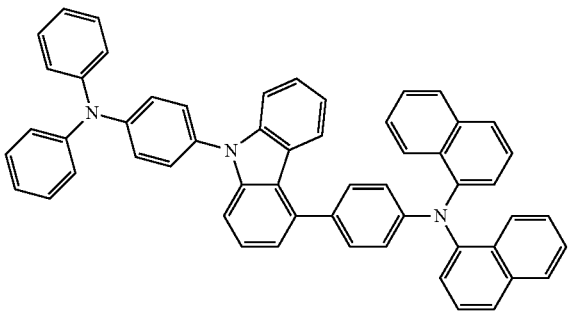
19
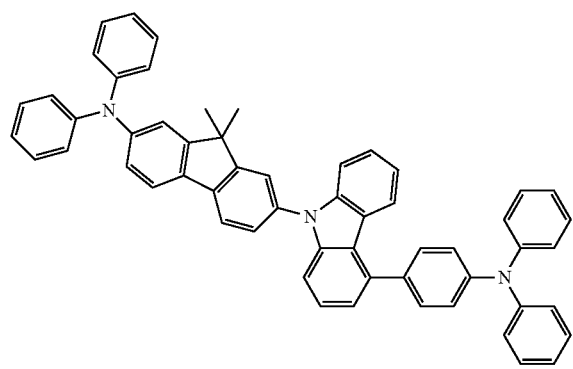
20
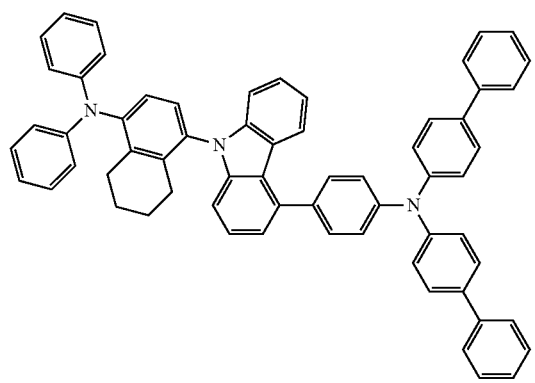
21
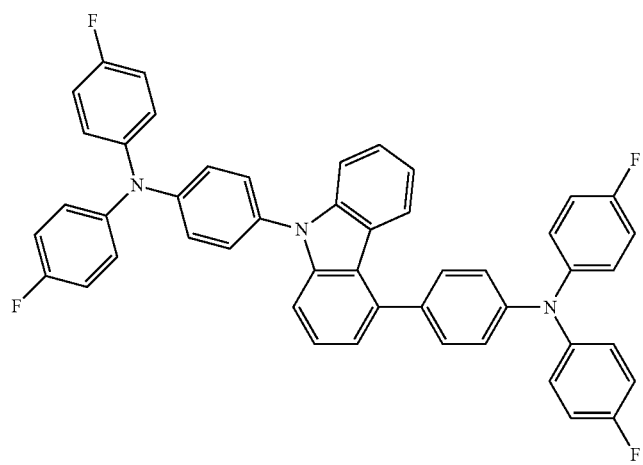
22
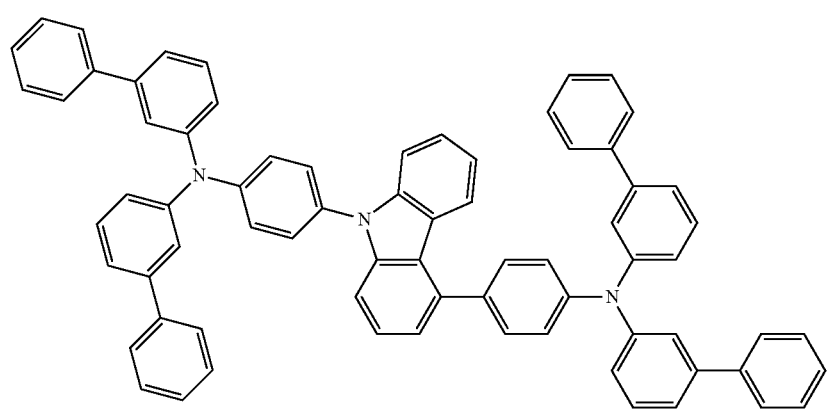

-continued
23
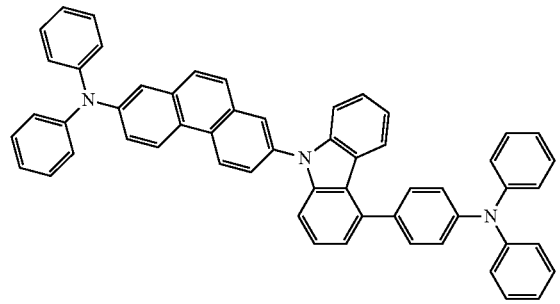
24
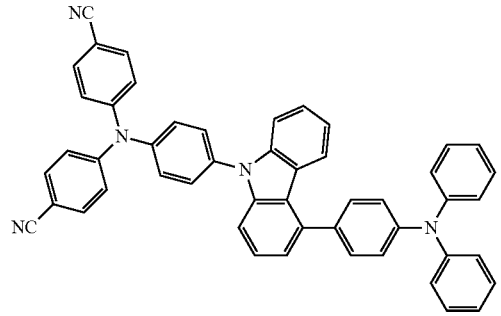
25
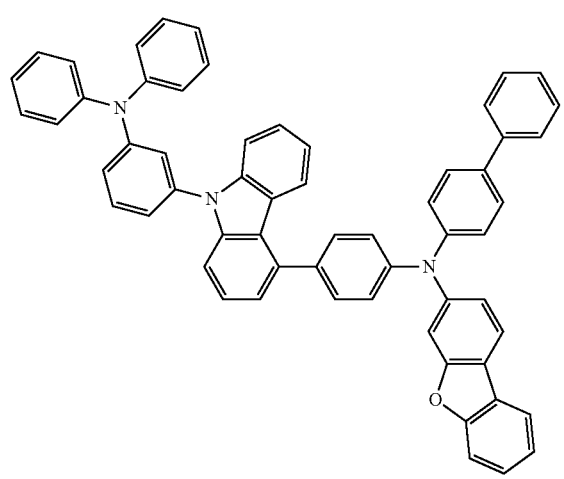
26
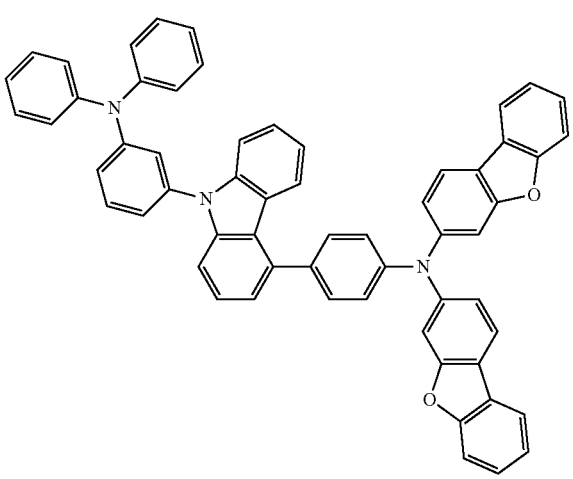
27
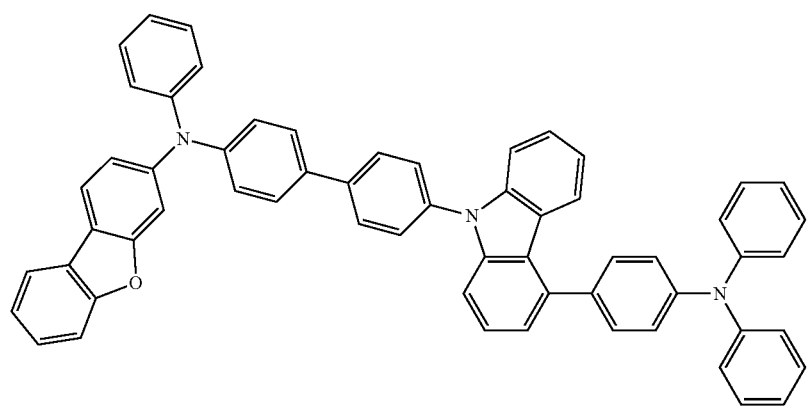

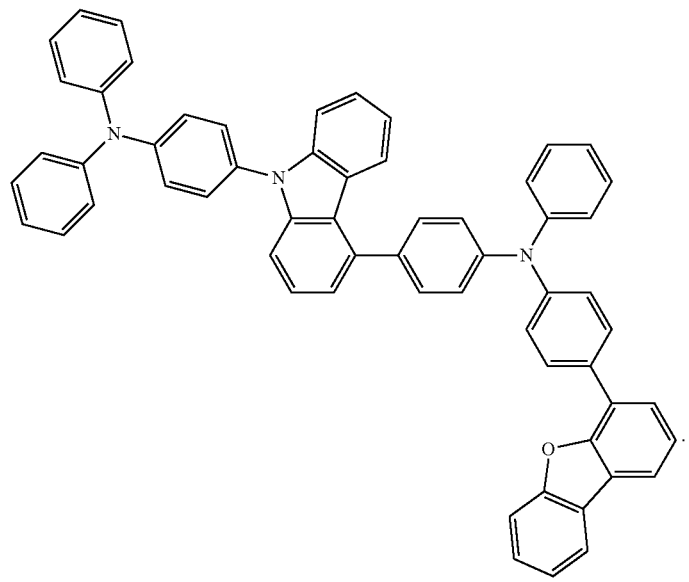

The carbazole compound according to the present embodiment has been described above in more detail. Since the carbazole compound according to the present embodiment has a very large band gap, the carbazole compound may have a high hole transporting ability and electron blocking ability. Thus, using the carbazole compound according to the present embodiment as a hole transport material may improve the emission efficiency of an organic electroluminescent device.

In the present disclosure, an aryl group may include, for example, a phenyl group, a biphenyl group, a terphenyl group, a naphthyl group, an anthryl group, a phenanthrenyl group, a fluorenyl group, an indenyl group, a pyrenyl group, a fluoranthenyl group, a triphenylenyl group, etc. An arylene group may refer to a divalent group in which one additional hydrogen of the aryl group is substituted.

In the present disclosure, a heteroaryl group may include, for example, a pyrazinyl group, a pyrrolyl group, a pyridyl group, a pyrimidyl group, a pyridazyl group, a furanyl group, a pyranyl group, a thienyl group, a quinolyl group, an isoquinolyl group, a benzofuranyl group, a benzothienyl group, an indolyl group, a benzoxazolyl group, a benzothiazolyl group, a quinoxalyl group, a benzoimidazolyl group, a pyrazolyl group, a tetrazolyl group, an imidazolyl group, an oxazolyl group, an isoxazolyl group, a thiazolyl group, an isothiazolyl group, a carbazolyl group, a dibenzofuranyl group, a dibenzothienyl group, etc.

In the present disclosure, an alkyl group may include, for example, a straight-chain (e.g., linear) alkyl group such as a methyl group, an ethyl group, a propyl group, a butyl group, an octyl group, a decyl group, a pentadecyl group, etc., and a branched chain (e.g., branched) alkyl group such as a t-butyl group, etc.

According to embodiments of the present disclosure, a material for use in organic electroluminescent devices may include the carbazole compound according to the foregoing embodiments. The material for use in organic electroluminescent devices may be included in any one of organic layers disposed (e.g., positioned) between electrodes in the organic electroluminescent device.

2. ORGANIC ELECTROLUMINESCENT DEVICE ACCORDING TO AN EMBODIMENT OF THE INVENTIVE CONCEPT

An organic electroluminescent device which includes a carbazole compound of an embodiment of the present disclosure will be described with reference to the drawing. The drawing is a schematic diagram illustrating an example of the organic electroluminescent device according to the present embodiment.

An organic electroluminescent device of an embodiment may include a substrate, a first electrode disposed (e.g., positioned) on the substrate, a second electrode disposed on the first electrode, and a plurality of lamination layers disposed between the first and second electrodes. At least one of the plurality of lamination layers may include the carbazole compound of the embodiment as described above.

As illustrated in the drawing, an organic electroluminescent device 100 according to the present embodiment includes a substrate 110, a first electrode 120 on the substrate 110, a hole injection layer 130 on the first electrode 120, a hole transport layer 140 on the hole injection layer 130, an emission layer 150 on the hole transport layer 140, an electron transport layer 160 on the emission layer 150, an electron injection layer 170 on the electron transport layer 160, and a second electrode 180 on the electron injection layer 170.

The carbazole compound according to the present embodiment may be included, for example, in the hole transport layer 140. However, the layer which includes the carbazole compound according to the present embodiment is not limited thereto. For example, the carbazole compound according to the present embodiment may be included in any one of the layers disposed between the first and second electrodes 120 and 180.

Any suitable substrate for an organic electroluminescent device may be used as the substrate 110. For example, the substrate 110 may be a glass substrate, a semiconductor substrate, a transparent plastic substrate, etc.

The first electrode 120 is disposed (e.g., positioned) on the substrate 110. The first electrode 120 may be, for example, an anode, and may be formed as a transmissive electrode using a metal, an alloy, or a conductive compound, which have a large work function. For example, the first electrode 120 may be formed of indium tin oxide (In$_2$O$_3$—SnO2: ITO), indium zinc oxide (In$_2$O$_3$—ZnO), tin oxide (SnO$_2$), zinc oxide (ZnO), etc., which are transparent and have good conductivity. In some embodiments, the first electrode 120 may be formed as a reflective electrode by laminating magnesium (Mg), aluminum (Al), etc., on the transparent conductive layer.

The hole injection layer 130 is disposed (e.g., positioned) on the first electrode 120. The hole injection layer 130 may facilitate the easy injection of holes from the first electrode 120 and may be formed to have a thickness of, for example, about 10 nm to about 150 nm. The hole injection layer 130, for example, may include one or more of compounds represented by the following structural formulae and collectively denoted as Formula 8:

Formula 8

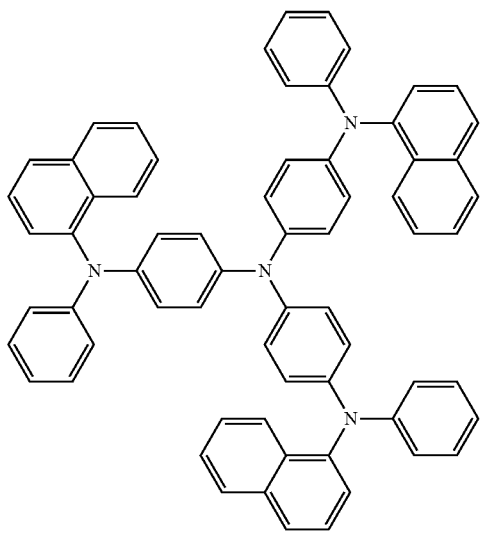

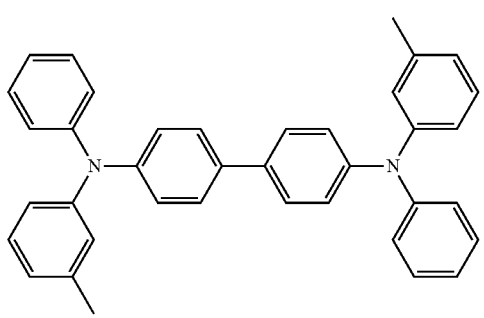

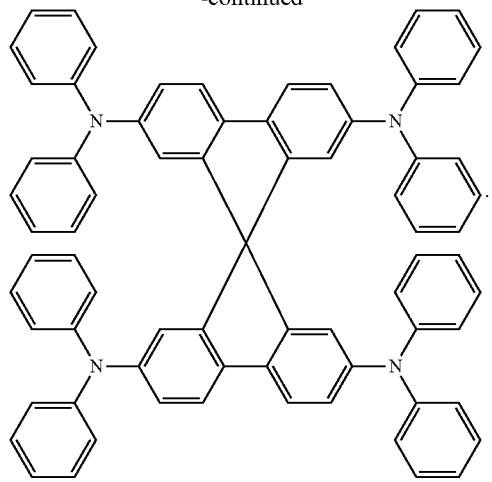

In some embodiments, the hole injection layer 130 may be formed of any suitable hole injection material. Non-limiting examples of suitable hole injection materials for forming the hole injection layer 130 may include triphenylamine-containing poly ether ketone (TPAPEK), 4-isopropyl-4'-methyldiphenyliodoniumtetrakis(pentafluorophenyl)borate (PPBI), N,N'-diphenyl-N,N'-bis-[4-(phenyl-m-tolyl-amino)-phenyl]-biphenyl-4,4'-diamine (DNTPD), a phthalocyanine compound such as copper phthalocyanine, 4,4',4"-tris(3-methylphenylphenylamino)triphenylamine (m-MTDATA), N,N'-di(1-naphthyl)-N,N'-diphenylbenzidine (NPB), 4,4',4"-tris{N,N-diphenylamino}triphenylamine (TDATA), 4,4',4"-tris(N,N-2-naphthylphenylamino)triphenylamine (2-TNATA), polyaniline/dodecylbenzenesulfonic acid (PANI/DBSA), poly(3,4-ethylenedioxythiophene)/poly(4-styrenesulfonate (PEDOT/PSS), polyaniline/camphorsulfonic acid (PANI/CSA), polyaniline/poly(4-styrenesulfonate (PANI/PSS), etc.

The hole transport layer 140 is disposed (e.g., positioned) on the hole injection layer 130. The hole transport layer 140 may facilitate the transport of holes and may be formed to have a thickness of, for example, about 10 nm to about 150 nm. In some embodiments, the hole transport layer 140 may be formed of multiple layers.

For example, the hole transport layer 140 may be formed to include the carbazole compound of an embodiment of the present disclosure. However, in the embodiments where the carbazole compound according to the present embodiment is included in another layer, the hole transport layer 140 may be formed of any suitable hole transport material. Non-limiting examples of suitable hole transport materials may include 1,1-bis[(di-4-tolylamino)phenyl]cyclohexane (TAPC); a carbazole derivative such as N-phenyl carbazole and/or polyvinyl carbazole; N,N'-bis(3-methylphenyl)-N, N'-diphenyl-[1,1-biphenyl]-4,4'-diamine (TPD); 4,4',4"-tris (N-carbazolyl)triphenylamine (TCTA); N,N'-di(1-naphthyl)-N,N'-diphenylbenzidine (NPB), etc.

The emission layer 150 is disposed (e.g., positioned) on the hole transport layer 140. The emission layer 150 may emit light through fluorescence, phosphorescence, etc. and may be formed to have a thickness of, for example, about 10 nm to about 60 nm. The emission layer 150 may be formed as, for example, a mixed layer of dopant and host materials. For example, the emission layer 150 may be formed as a mixed layer in which a doping amount of the dopant material is about 0.1% to about 50% by mass based on the total mass of the host material.

The dopant material may be, for example, a compound selected from compounds represented by the following structural formulae and collectively denoted as Formula 9:
Formula 9
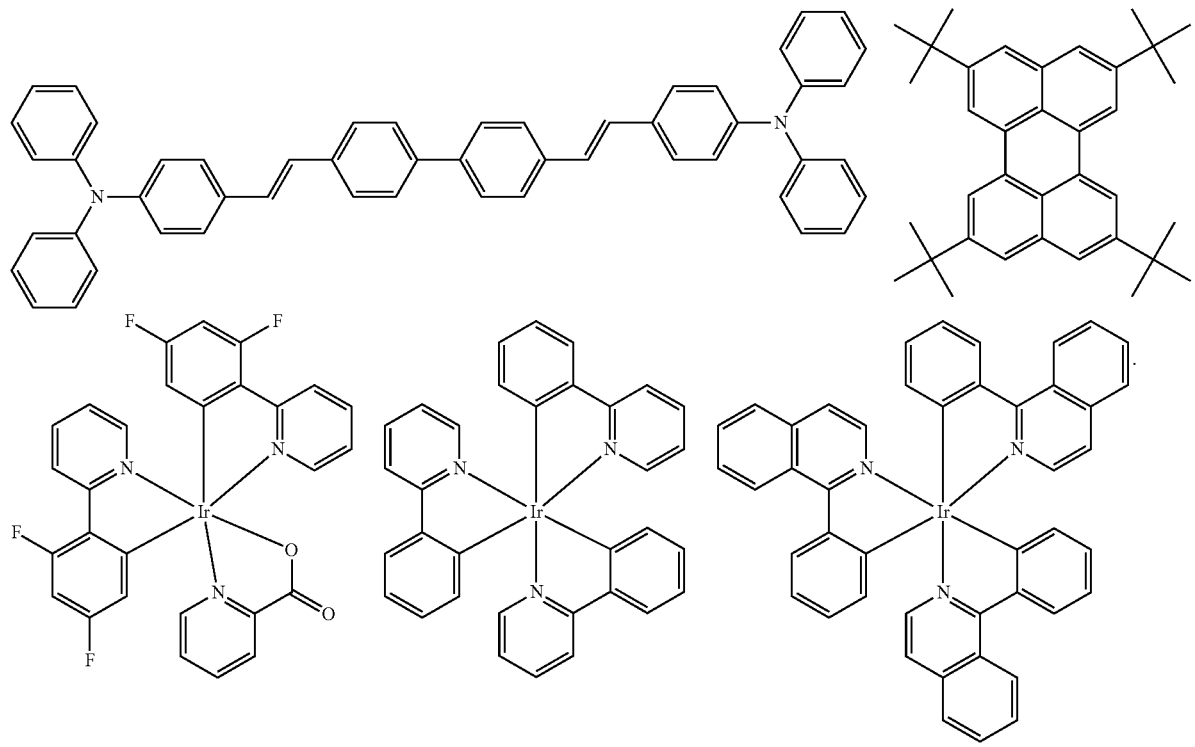
The host material may be, for example, a compound selected from compounds represented by the following structural formulae and collectively denoted as Formula 10:
Formula 10
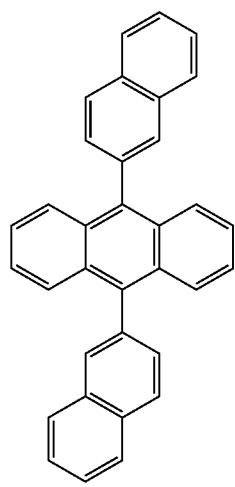
-continued
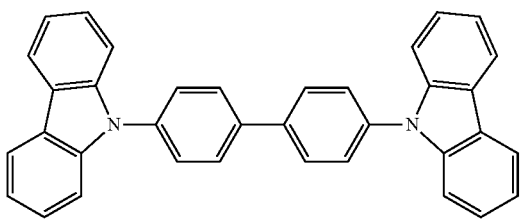
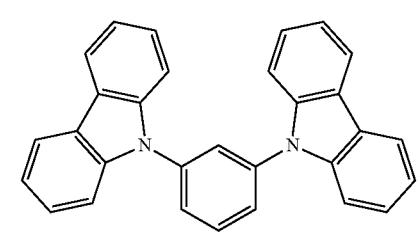

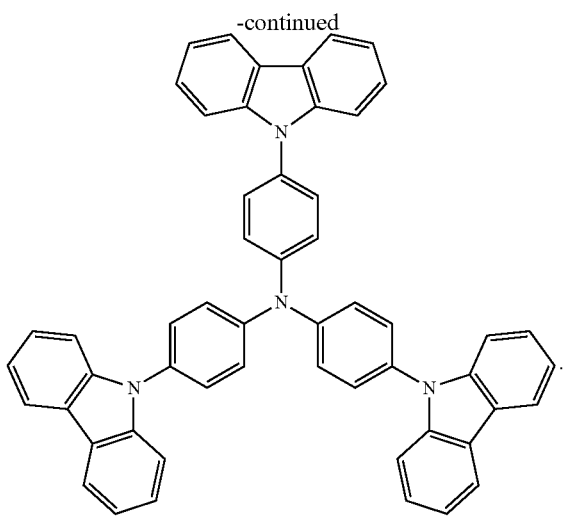

In some embodiments, the emission layer 150 may be formed of any suitable light-emitting material. Non-limiting examples of suitable light-emitting materials may include a fluoranthene derivative, a styryl derivative, a pyrene derivative, an arylacetylene derivative, a fluorene derivative, a perylene derivative, a chrysene derivative, etc. For example, the emission layer 150 may also be formed of a styryl derivative, a pyrene derivative, a perylene derivative, and/or an anthracene derivative.

For example, an anthracene derivative represented by the following Formula 11 may be used as the light-emitting material of the emission layer 150:

Formula 11

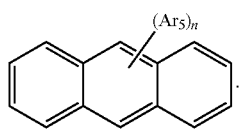

In the above Formula 11, $Ar_5$ may be selected from hydrogen, deuterium, a substituted or unsubstituted alkyl group having 1 to 50 carbon atoms for forming a ring, a substituted or unsubstituted cycloalkyl group having 3 to 50 carbon atoms for forming a ring, a substituted or unsubstituted alkoxy group having 1 to 50 carbon atoms for forming a ring, a substituted or unsubstituted aralkyl group having 7 to 50 carbon atoms for forming a ring, a substituted or unsubstituted aryloxy group having 6 to 50 carbon atoms for forming a ring, a substituted or unsubstituted arylthio group having 6 to 50 carbon atoms for forming a ring, a substituted or unsubstituted alkoxycarbonyl group having 2 to 50 carbon atoms for forming a ring, a substituted or unsubstituted aryl group having 6 to 50 carbon atoms for forming a ring, a substituted or unsubstituted silyl group having 5 to 50 carbon atoms for forming a ring, a carboxyl group, a halogen atom, a cyano group, a nitro group, and a hydroxyl group; and n may be an integer from 1 to 10.

In some embodiments, $Ar_5$ may be selected from a phenyl group, a biphenyl group, a terphenyl group, a naphthyl group, anthryl group, a phenanthryl group, a fluorenyl group, an indenyl group, a pyrenyl group, an acetonaphthenyl group, a fluoranthenyl group, a triphenylenyl group, a pyridyl group, a furanyl group, a pyranyl group, a thienyl group, a quinolyl group, a isoquinolyl group, a benzofuranyl group, a benzothienyl group, an indolyl group, a carbazolyl group, a benzoxazolyl group, a benzothiazolyl group, a quinoxalyl group, a pyrazolyl group, a dibenzofuranyl group, a dibenzothienyl group, etc. For example, $Ar_5$ may be selected from a phenyl group, a biphenyl group, a terphenyl group, a fluorenyl group, a carbazolyl group, a dibenzofuranyl group, etc.

The anthracene derivative represented by the above Formula 11 may be selected from, for example, compounds a-1 to a-12 represented by the following structural formulae and collectively denoted as Formula 12. However, the compound represented by Formula 11 is not limited to the following compounds a-1 to a-12.

Formula 12

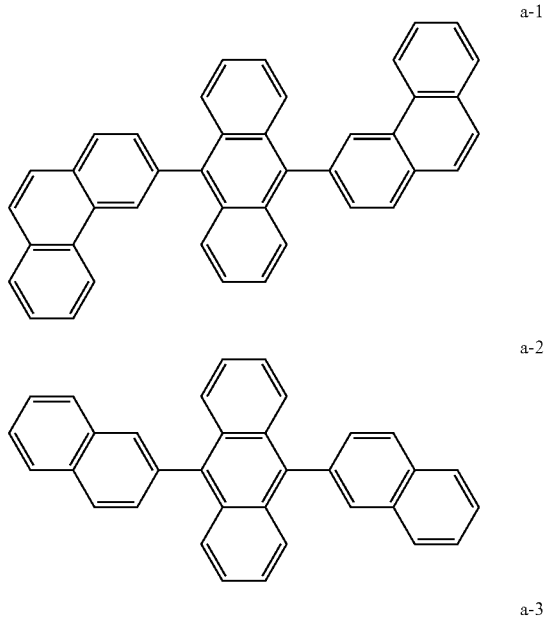

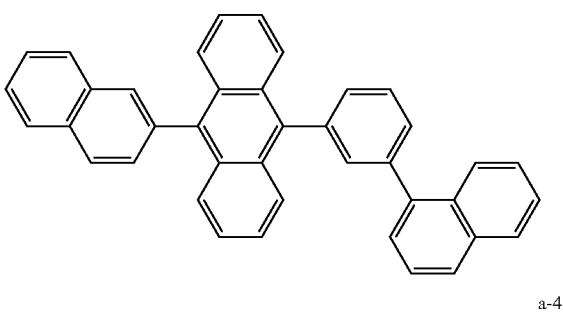

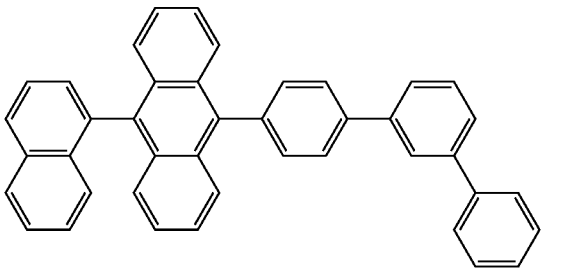

a-5
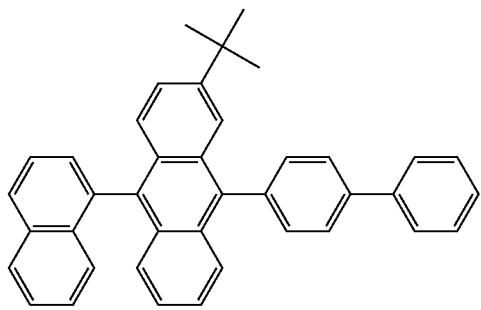

a-6
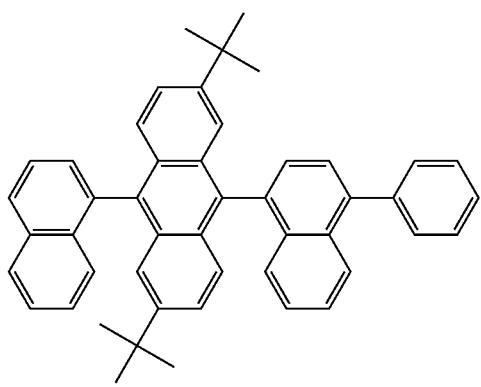

a-7
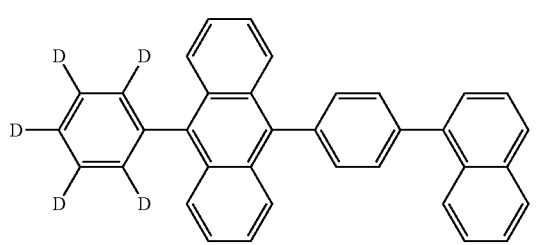

a-8
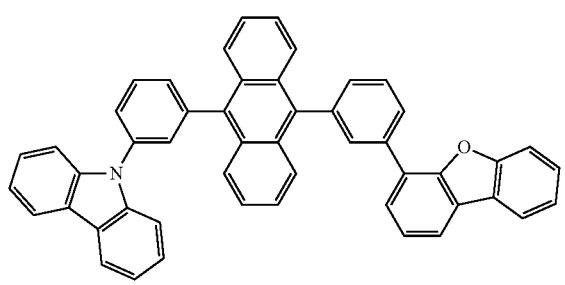

a-9
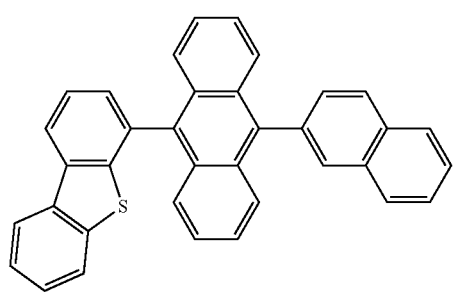

a-10
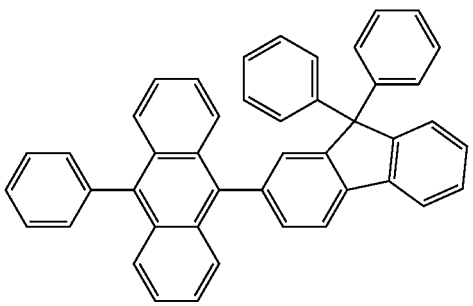

a-11
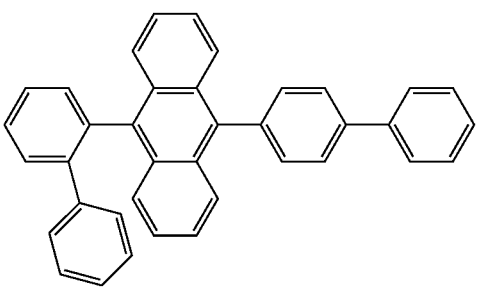

a-12
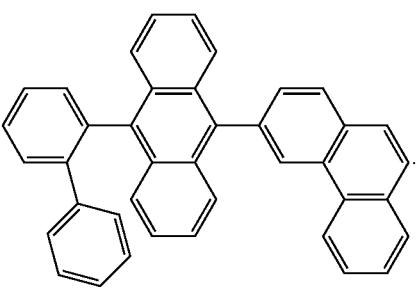

In some embodiments, the emission layer 150 may be formed of a styryl derivative such as 1,4-bis[2-(3-N-ethyl-carbazoryl)vinyl]benzene (BCzVB), 4-(di-p-tolylamino)-4'-[(di-p-tolylamino)styryl]stilbene (DPAVB), N-(4-((E)-2-(6-((E)-4-(diphenylamino)styryl)naphthalen-2-yl)vinyl)phenyl)-N-phenylbenzenamine (N-BDAVBi), etc. The emission layer 150 may also be formed of, for example, a perylene derivative (such as 2,5,8,11-tetra-t-butylperylene (TBPe), etc.) or a pyrene derivative (such as 1,1-dipyrene, 1,4-dipyrenylbenzene, 1,4-bis(N,N-diphenylamino)pyrene, etc.) However, the embodiment of the present inventive concept is not limited by the above example compounds.

The electron transport layer 160 is disposed (e.g., positioned) on the emission layer 150. The electron transport layer 160 may facilitate the transport of electrons and may be formed to have a thickness, for example, of about 15 nm to about 50 nm. The electron transport layer 160 may be formed of, for example, any of compounds represented by the following structural formulae and collectively denoted as Formula 13:

Formula 13

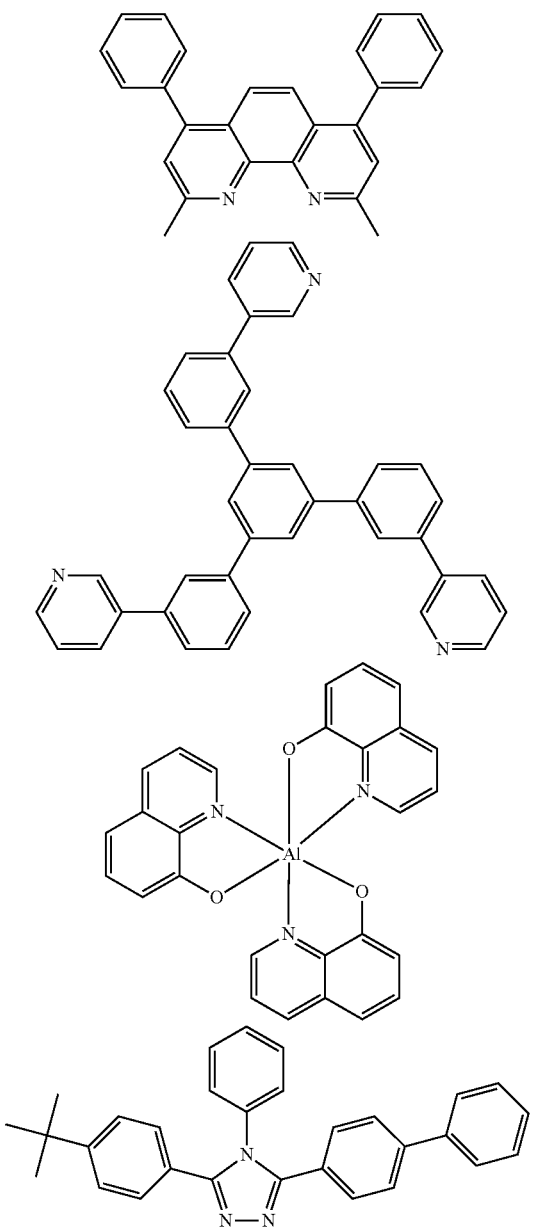

The electron transport layer 160 may be formed of any suitable electron transport material. Non-limiting examples of suitable electron transport materials may include tris(8-hydroxyquinolinato)aluminum (Alq3), a compound which has a nitrogen-containing aromatic ring, etc. Non-limiting examples of the compound which has a nitrogen-containing aromatic ring may include a compound which has a pyridine ring, such as 1,3,5-tri[(3-pyridyl)-phen-3-yl]benzene; a compound which has a triazine ring, such as 2,4,6-tris(3'-(pyridin-3-yl)biphenyl-3-yl)-1,3,5-triazine; a compound which has an imidazole ring, such as 2-(4-(N-phenylbenzoimidazolyl-1-ylphenyl)-9,10-dinaphthylanthracene; etc.

The electron injection layer 170 is disposed (e.g., positioned) on the electron transport layer 160. The electron injection layer 170 may facilitate the easy injection of electrons from the second electrode 180, and may be formed to have a thickness of about 0.3 nm to about 9 nm. Any material suitable for forming an electron injection layer may be used for the electron injection layer 170. For example, the electron injection layer 170 may be formed of a lithium (Li) complex (such as lithium 8-quinolinolato (Liq), lithium fluoride (LiF), etc.), sodium chloride (NaCl), cesium fluoride (CsF), lithium oxide ($Li_2O$), barium oxide (BaO), etc.

The second electrode 180 is disposed (e.g., positioned) on the electron injection layer 170. The second electrode 180 may be, for example, a cathode, and may be formed as a reflective electrode using a metal, an alloy, or a conductive compound, which have a low work function. The second electrode 180 may also be formed of, for example, a metal such as lithium (Li), magnesium (Mg), aluminum (Al), calcium (Ca), etc., or a mixture of metals such as aluminum-lithium (Al—Li), magnesium-indium (Mg—In), magnesium-silver (Mg—Ag), etc. In some embodiments, the second electrode 180 may be formed as a transmissive electrode using a thin film of the metal material having a thickness up to about 20 nm, or using a transparent conductive film such as indium tin oxide, indium zinc oxide, etc.

Each of the above-described layers may be formed by one or more suitable film forming methods, such as vacuum deposition, sputtering, various coating methods, etc., selected according to the material to be used in each layer. The organic layers disposed (e.g., positioned) between the first electrode 120 and the second electrode 180 may each independently be formed, for example, through various suitable deposition methods, various coating methods, etc. The metal layers (such as the first electrode 120 and the second electrode 180) may each independently be formed, for example, through vacuum deposition, sputtering, etc.

An example of the organic electroluminescent device 100 according to the present embodiment has been described hereinabove. The organic electroluminescent device 100 according to the present embodiment may include the carbazole compound represented by Formula 1, and may have improved emission efficiency.

However, the lamination structure of the organic electroluminescent device 100 according to the present embodiment is not limited to the example as described above. The organic electroluminescent device 100 according to the present embodiment may also be provided to have another suitable lamination structure. For example, the organic electroluminescent device 100 may exclude at least one selected from the hole injection layer 130, the hole transport layer 140, the electron transport layer 160, and the electron injection layer 170. In some embodiments, the organic electroluminescent device 100 may include other additional layers. Each layer which is included in the organic electroluminescent device 100 may be formed as a single layer, or as multiple layers (e.g., to have a single-layer or a multi-layer structure).

The organic electroluminescent device 100 may also include a hole blocking layer between the electron transport layer 160 and the emission layer 150 to prevent or reduce the diffusion of triplet excitons and holes into the electron transport layer 160. The hole blocking layer may be formed of, for example, an oxadiazole derivative, a triazole derivative, a phenanthroline derivative, etc.

3. EXAMPLES

Hereinafter, a carbazole compound according to the present embodiment, and an organic electroluminescent device including the carbazole compound will be described in more detail with reference to Examples and Comparative Examples. However, the Examples provided below are for illustrative purposes only, and the carbazole compound according to the present embodiment and the organic electroluminescent device including the carbazole compound are not limited to these Examples.

3.1. Synthesis of Carbazole Compound

A method of synthesizing the carbazole compound according to the present embodiment will be described by showing example methods of synthesizing Compounds 12 and 15. However, methods of synthesizing carbazole compounds according to the present embodiments are not limited to examples provided below.

3.1.1. Synthesis of Compound 12

Compound 12, an example of a carbazole compound according to the present embodiment, was synthesized using the following acts.

First, under an argon (Ar) atmosphere, 3.16 g of 4-bromo-9H-carbazole, 4.77 g of 4-(diphenylamino)phenylboronic acid pinacol ester, 225 mL of toluene, 4.9 g of potassium phosphate ($K_3PO_4$), 0.93 g of tetrakis(triphenylphosphine)palladium(0) ($Pd(PPh_3)_4$), 18 mL of ethanol, and 30 mL of water were added, in the stated order, into a 500 mL three-necked flask, followed by heating and refluxing the resultant mixture at 90° C. for 10 hours. The solid thus obtained was purified through flash column chromatography to obtain 4.8 g (Yield 92%) of a white, solid intermediate product 1.

Next, under an argon (Ar) atmosphere, 4.8 g of the intermediate product 1, 5.3 g of 3-bromobiphenylyl)diphenylamine, 200 mL of toluene, 0.27 g of tris(dibenzylideneacetone)dipalladium(0) ($Pd_2(dba)_3$), 6.9 g of sodium-t-butoxide (t-BuONa), 250 mL of dry toluene, and 0.9 mL of a 2 M solution of tri(t-butyl)phosphine were added, in the stated order, into a 500 mL three-necked flask, followed by stirring the resultant mixture at 60° C. for 12 hours. Water was added to the reaction mixture, the resultant mixture was then extracted using dichloromethane, and the organic layer thus extracted was solidified through evaporation. The solid thus obtained was purified through flash column chromatography to obtain 4.3 g (Yield 50%) of the white, solid Compound 12.

The obtained target compound was analyzed using $^1$HNMR (1H Nuclear Magnetic Resonance: 300 MHz, $CDCl_3$, ppm), and the measured chemical shift values (δ) were 7.0-7.2 (m, 5H), 7.2-7.38 (m, 15H), 7.4-7.45 (m, 3H), 7.46-7.56 (m, 5H), 7.64 (t, 1H), 7.69 (dt, 1H), 7.74 (d, 1H), 7.77 (t, 1H). In addition, the obtained target compound was also analyzed using FAB-MS (Fast Atom Bombardment-Mass Spectrometry), and the measured molecular weight was 729. The results confirmed the obtained target compound as being Compound 12.

3.1.2. Synthesis of Compound 15

Compound 15, an example of a carbazole compound according to the present embodiment, was synthesized through the following procedure.

First, intermediate product 2 was synthesized using the same (or substantially the same) method as the one used in the synthesis of the intermediate product 1, except that 3-(diphenylamino)phenylboronic acid pinacol ester was used instead of 4-(diphenylamino)phenylboronic acid pinacol ester. 4.9 g (Yield 94%) of a white, solid intermediate product 2 were obtained.

Next, under an argon (Ar) atmosphere, 4.8 g of the intermediate product 2, 4.3 g of 4-bromophenyl)diphenylamine, 200 mL of toluene, 0.27 g of tris(dibenzylideneacetone)dipalladium(0), 6.9 g of sodium-t-butoxide, 250 mL of dry toluene, and 0.9 mL of a 2 M solution of tri(t-butyl)phosphine were added, in the stated order, into a 500 mL three-necked flask, followed by stirring the resultant mixture at 60° C. for 12 hours. Water was added to the reaction mixture, the resultant mixture was then extracted using dichloromethane, and the organic layer thus extracted was solidified through evaporation. The solid thus obtained was purified through flash column chromatography to obtain 4.7 g (Yield 60%) of the white, solid Compound 15.

The obtained target compound was analyzed using $^1$HNMR and FAB-MS. The molecular weight measured using FAB-MS was 653. The results confirmed the obtained target compound as being Compound 15.

3.2. Manufacturing of Organic Electroluminescent Device

A blue light-emitting organic electroluminescent device which includes the carbazole compound according to the present embodiment was manufactured through the following acts by using vacuum deposition.

3.2.1. Example 1

First, surface treatment using ultra-violet radiation and ozone ($O_3$) was performed on an ITO-glass substrate which was subjected to patterning and cleaning. In addition, an ITO layer (herein, a first electrode) on an ITO-glass substrate may have a thickness of about 150 nm. The surface-treated substrate was placed inside a deposition apparatus for forming an organic film, in which a hole injection layer, a hole transport layer (HTL), an emission layer, and an electron transport layer were successively laminated under a vacuum level of about $10^{-4}$ to about $10^{-5}$ Pa.

The hole injection layer was formed of 4,4',4"-tris(N,N-2-naphthylphenylamino)triphenylamine (2-TNATA) to have a thickness of about 60 nm. The hole transport layer (HTL) was formed of the Compound 12 to have a layer thickness of about 30 nm. The emission layer was formed using 9,10-di(2-naphthyl)anthracene (ADN) as a host material and 2,5,8,11-tetra-t-butylperylene (TBP) as a dopant material, to have a layer thickness of about 25 nm. A doping amount of the dopant material was about 3% by mass based on the total mass of the host material. The electron transport layer was formed of Alq3 to have a thickness of about 25 nm.

Next, the substrate was transferred to the deposition apparatus for forming metal layers, and an electron injection layer and a second electrode were deposited thereon under a vacuum level of about $10^{-4}$ to about $10^{-5}$ Pa, thus completing the manufacture of an organic electroluminescent device. The electron injection layer was formed of lithium fluoride (LiF) to have a layer thickness of about 1 nm, and the second electrode was formed of aluminum (Al) to have a layer thickness of about 100 nm.

3.2.2. Example 2

An organic electroluminescent device was manufactured using the same (or substantially the same) method as the manufacturing method of Example 1 except a hole transport layer was formed using Compound 15 instead of Compound 12.

The structures of Compounds 12 and 15 are shown below and collectively denoted as Formula 14.

Formula 14

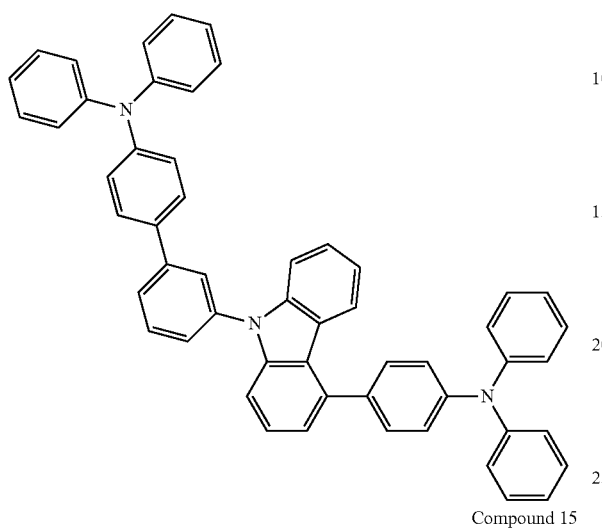

Compound 12

Compound 15

3.2.3. Comparative Example 1

An organic electroluminescent device was manufactured using the same (or substantially the same) method as the manufacturing method of Example 1 except a hole transport layer was formed using Compound c1 instead of Compound 12. In Compound c1 (illustrated below), only position 3 of a carbazole ring is substituted with an arylamino group.

3.2.4. Comparative Example 2

An organic electroluminescent device was manufactured using the same (or substantially the same) method as the manufacturing method of Example 1 except a hole transport layer was formed using Compound c2 instead of Compound 12. In Compound c2 (illustrated below), an arylamino group is substituted only at position 4 of the carbazole ring (or position 5, if carbon positions in the carbazole ring are assigned counterclockwise).

3.2.5 Comparative Example 3

An organic electroluminescent device was manufactured using the same (or substantially the same) method as the manufacturing method of Example 1 except a hole transport layer was formed using Compound c3, instead of Compound 12. In Compound c3 (illustrated below), positions 3 and 9 in the carbazole ring are substituted with arylamino groups.

Formula 15

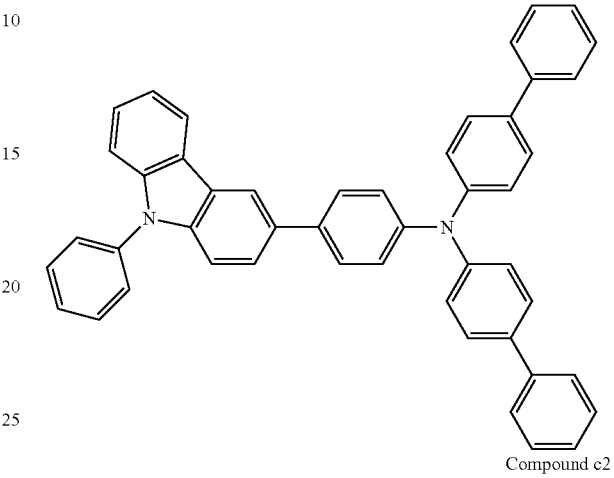

Compound c1

Compound c2

Compound c3

3.3. Evaluation Results

Evaluation results of the organic electroluminescent devices which were manufactured according to Examples 1 and 2, and Comparative Examples 1 to 3 are shown in the following Table 1. A C9920-11 luminance distribution characteristic measuring device (produced by HAMAMATSU Photonics) was used in the evaluation of the electroluminescent properties of the manufactured organic electroluminescent devices 100. The results which are shown in the following Table 1 were measured at a current density of about 10 mA/cm$^2$.

TABLE 1

| | HTL | Operating Voltage [V] | Emission Efficiency (cd/A) |
|---|---|---|---|
| Example 1 | Compound 12 | 7.9 | 7.1 |
| Example 2 | Compound 15 | 8.1 | 6.9 |
| Comparative Example 1 | Compound c1 | 7.5 | 5.2 |
| Comparative Example 2 | Compound c2 | 8.1 | 6.2 |
| Comparative Example 3 | Compound c3 | 7.8 | 4.7 |

Referring to the results in Table 1, it can be seen that in Examples 1 and 2, in which the carbazole compound according to the present embodiment was used in the hole transport layer, the emission efficiency could be improved without substantially increasing the operating voltage, as compared to Comparative Examples 1 to 3.

For example, it can be seen that the organic electroluminescent devices of Examples 1 and 2 had improved emission efficiency, when compared to Comparative Examples 1 and 2 respectively using Compounds c1 and c2, which did not include an arylamino group at position 9 of the carbazole ring. In addition, it can also be seen that the organic electroluminescent devices of Examples 1 and 2 (using compounds which included arylamino groups at positions 4 and 9 positions of the carbazole ring) had improved emission efficiency, when compared to Comparative Example 3 using Compound c3, which included arylamino groups at positions 3 and 9 positions of the carbazole ring.

According to embodiments of the present disclosure, a carbazole compound including arylamino groups coupled at positions 4 and 9 of the carbazole ring may improve the emission efficiency of an organic electroluminescent device.

The carbazole compound according to the present embodiment may be represented by the above-described Formula 1, and may improve the emission efficiency of an organic electroluminescent device which uses the carbazole compound. The carbazole compound according to the present embodiment may be used as a material in an organic electroluminescent device, for example, may be used as a hole transport material.

As described above, according to embodiments of the present inventive concept, the emission efficiency of an organic electroluminescent device may be improved.

As used herein, expressions such as "at least one of," "one of," "at least one selected from," and "one selected from," when preceding a list of elements, modify the entire list of elements and do not modify the individual elements of the list. Further, the use of "may" when describing embodiments of the present invention refers to "one or more embodiments of the present invention."

In addition, as used herein, the terms "use," "using," and "used" may be considered synonymous with the terms "utilize," "utilizing," and "utilized," respectively.

As used herein, the terms "substantially," "about," and similar terms are used as terms of approximation and not as terms of degree, and are intended to account for the inherent deviations in measured or calculated values that would be recognized by those of ordinary skill in the art.

Also, any numerical range recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

The above-disclosed subject matter is to be considered illustrative and not restrictive, and the appended claims and equivalents thereof are intended to cover all such modifications, enhancements, and other embodiments, which fall within the true spirit and scope of the present inventive concept. Thus, to the maximum extent allowed by law, the scope of the present inventive concept is to be determined by the broadest permissible interpretation of the following claims and their equivalents, and shall not be restricted or limited by the foregoing detailed description.

What is claimed is:

1. A carbazole compound represented by Formula 1:

Formula 1

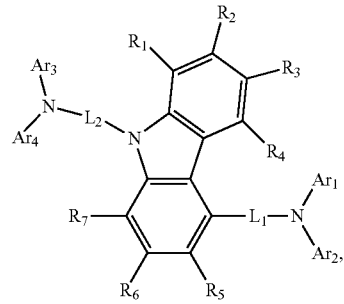

wherein, in Formula 1, $R_1$ to $R_7$ are each independently selected from hydrogen, a halogen atom, a hydroxyl group, a cyano group, a nitro group, an alkoxy group, an aryloxy group, an alkyl or aryl substituted silyl group, a substituted or unsubstituted alkyl group, a substituted or unsubstituted aryl group, and a substituted or unsubstituted heteroaryl group;

$Ar_1$ to $Ar_4$ are each independently selected from a substituted or unsubstituted alkyl group, a substituted or unsubstituted aryl group, and a substituted or unsubstituted heteroaryl group;

L₁ is a substituted or unsubstituted arylene group; and

L₂ is selected from a single bond and a substituted or unsubstituted arylene group.

2. The carbazole compound of claim 1, wherein at least one selected from L₁ and L₂ is a substituted or unsubstituted connecting group selected from the following groups collectively denoted as Formula 2:

Formula 2

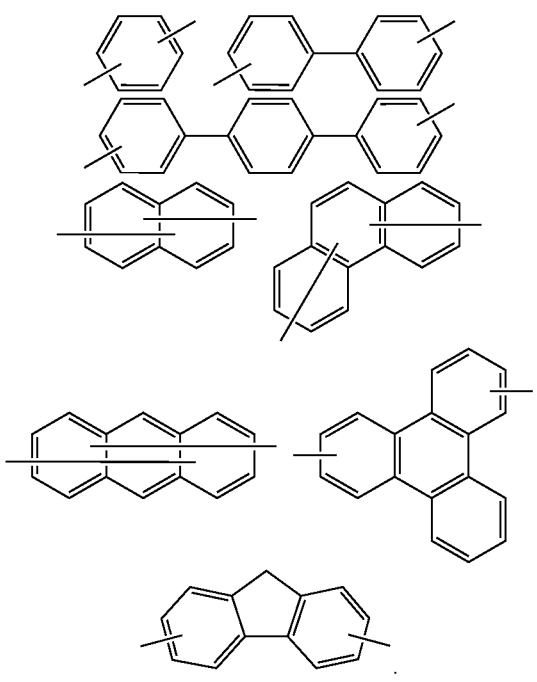

3. The carbazole compound of claim 1, wherein at least one selected from L₁ and L₂ is a substituted or unsubstituted connecting group selected from the following groups collectively denoted as Formula 3:

Formula 3

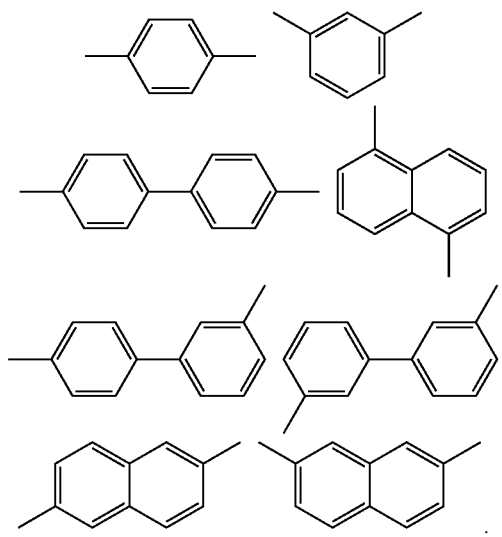

4. The carbazole compound of claim 1, wherein at least one selected from L₁ and L₂ is a substituted or unsubstituted connecting group selected from the following groups collectively denoted as Formula 4:

Formula 4

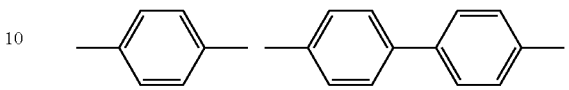

5. The carbazole compound of claim 1, wherein the Ar₁ to Ar₄ are each independently a substituted or unsubstituted aryl group or a substituted or unsubstituted heteroaryl group selected from the following groups collectively denoted as Formula 5:

Formula 5

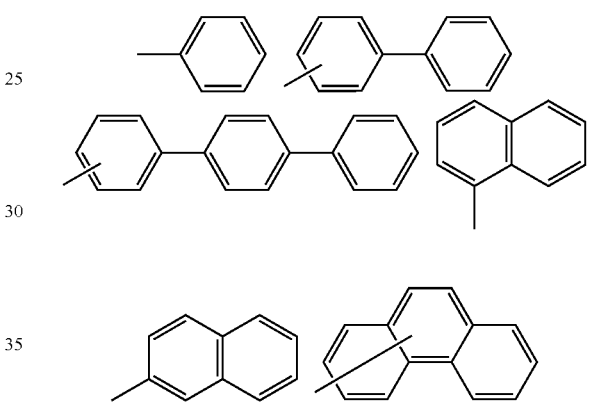

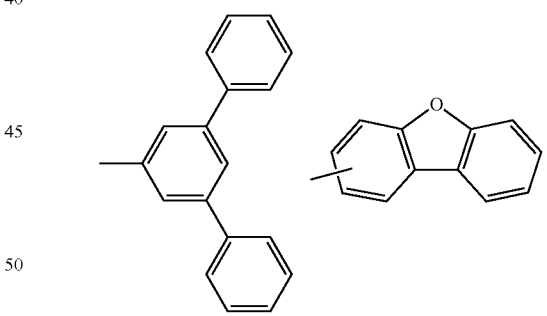

6. The carbazole compound of claim 5, wherein the Ar₁ to Ar₄ each independently comprise up to 14 carbon atoms for forming a ring.

7. The carbazole compound of claim 1, wherein the R₁ to R₇ are each independently selected from hydrogen, a fluorine atom, a cyano group, a methyl group, and a phenyl group.

8. The carbazole compound of claim 1, wherein the carbazole compound has a molecular weight of 500 to 1,000.

9. The carbazole compound of claim 1, wherein the carbazole compound is selected from Compounds 1, 2, 9, and 11 to 13

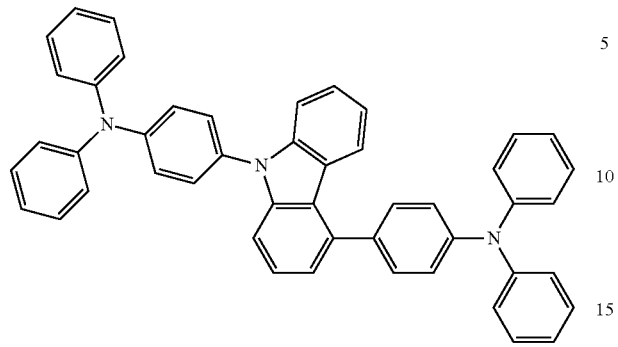
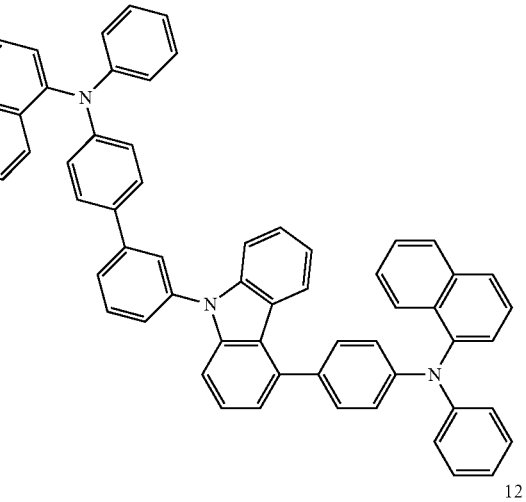
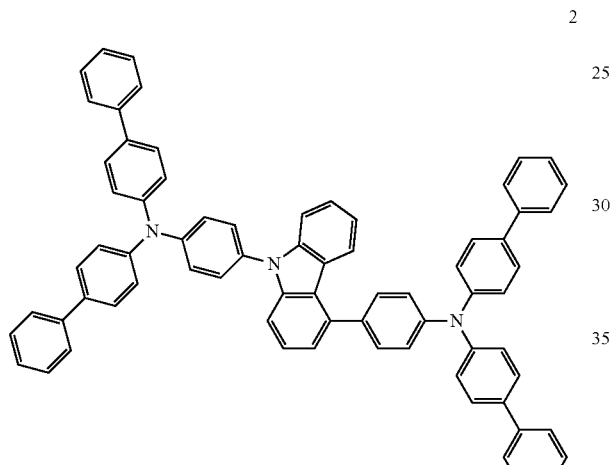
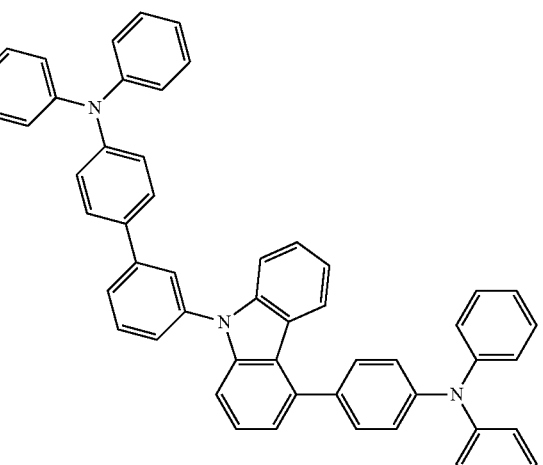
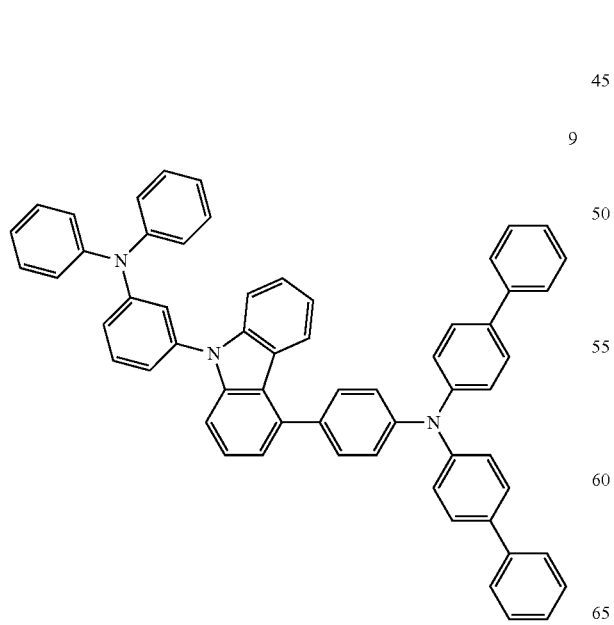
10. A material for use in an organic electroluminescent device, the material comprising the carbazole compound of claim 1.
11. An organic electroluminescent device, comprising:
a substrate;
a first electrode on the substrate;
a second electrode on the first electrode; and a plurality of lamination layers between the first and second electrodes;

wherein at least one of the plurality of lamination layer's comprises a carbazole compound represented by Formula 1:

Formula 1

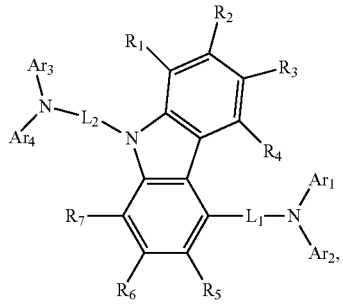

wherein, in Formula 1,

R₁ to R₇ are each independently selected from hydrogen, a halogen atom, a hydroxyl group, a cyano group, a nitro group, an alkoxy group, an aryloxy group, an alkyl or aryl substituted silyl group, a substituted or unsubstituted alkyl group, a substituted or unsubstituted aryl group, and a substituted or unsubstituted heteroaryl group;

Ar₁ to Ar₄ are each independently selected from a substituted or unsubstituted alkyl group, a substituted or unsubstituted aryl group, and a substituted or unsubstituted heteroaryl group; and L₁ is a substituted or unsubstituted arylene group; and L₂ is selected from a single bond and a substituted or unsubstituted arylene group.

12. The organic electroluminescent device of claim 11, wherein the plurality of lamination layers comprises a hole transport layer comprising the carbazole compound represented by Formula 1.

13. The organic electroluminescent device of claim 11, wherein at least one selected from L₁ and L₂ in Formula 1 is a substituted or unsubstituted connecting group selected from the following groups collectively denoted as Formula 2:

Formula 2

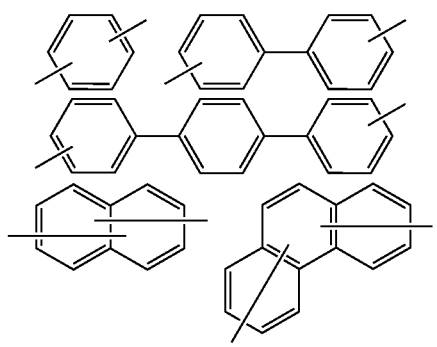

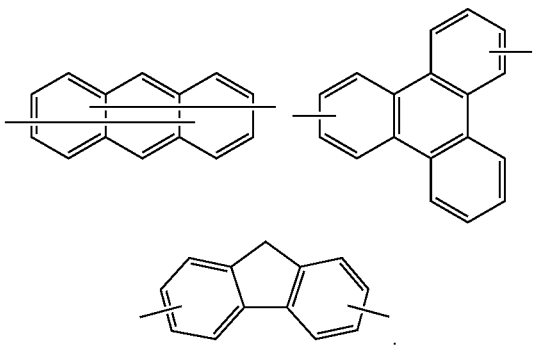

14. The organic electroluminescent device of claim 11, wherein at least one selected from L₁ and L₂ in Formula 1 is a substituted or unsubstituted connecting group selected from the following groups collectively denoted as Formula 3:

Formula 3

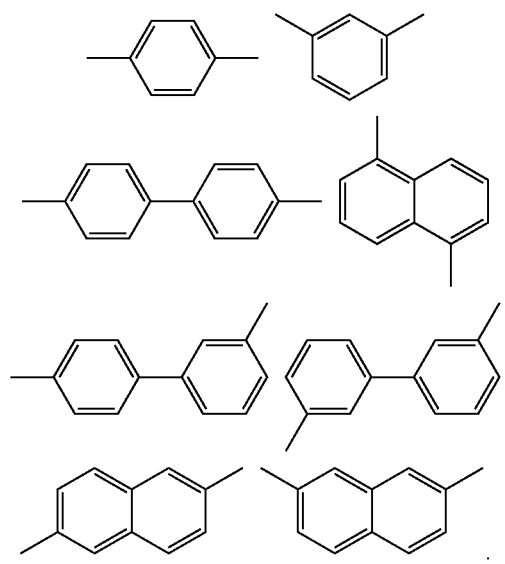

15. The organic electroluminescent device of claim 11, wherein at least one selected from L₁ and L₂ in Formula 1 is a substituted or unsubstituted connecting group selected from the following groups collectively denoted as Formula 4:

Formula 4

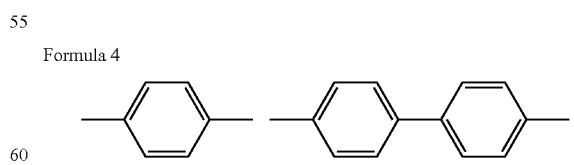

16. The organic electroluminescent device of claim 11, wherein the Ar₁ to Ar₄ in Formula 1 are each independently a substituted or unsubstituted aryl group or a substituted or unsubstituted heteroaryl group selected from the following groups collectively denoted as Formula 5:

Formula 5

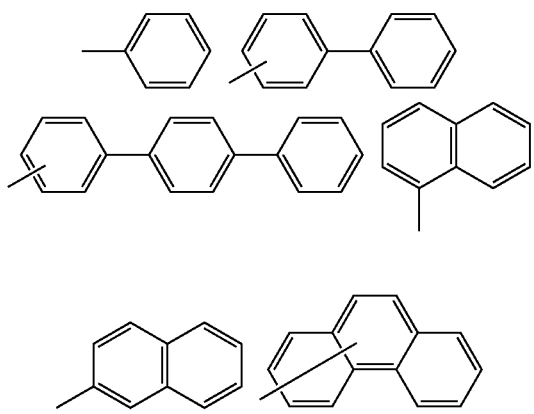

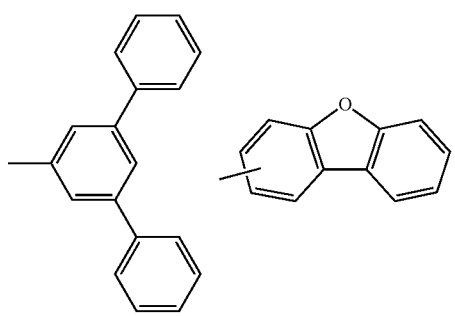

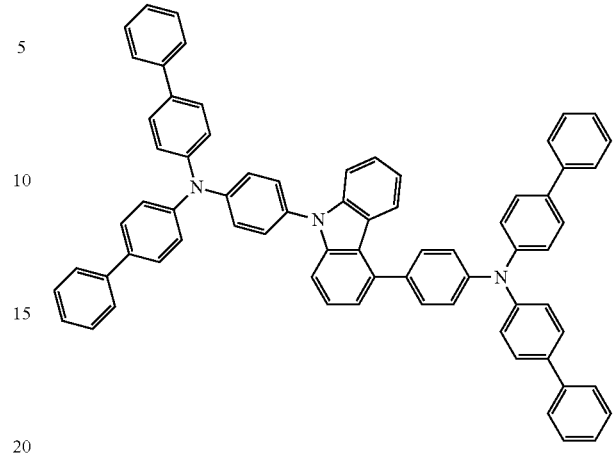

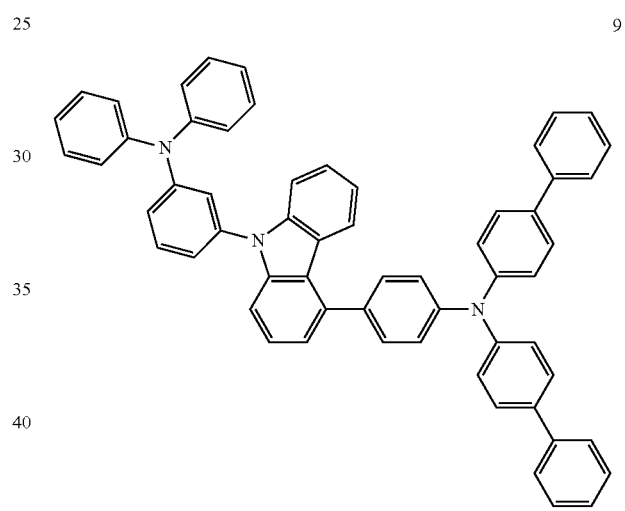

17. The organic electroluminescent device of claim 16, wherein the $Ar_1$ to $Ar_4$ each independently comprise up to 14 carbon atoms for forming a ring.

18. The organic electroluminescent device of claim 11, wherein the $R_1$ to $R_7$ are each independently selected from hydrogen, a fluorine atom, a cyano group, a methyl group, and a phenyl group.

19. The organic electroluminescent device of claim 11, wherein the carbazole compound represented by Formula 1 has a molecular weight of 500 to 1,000.

20. The organic electroluminescent device of claim 11, wherein the carbazole compound represented by Formula 1 is selected from Compounds 1, 2, 9, and 11 to 13:

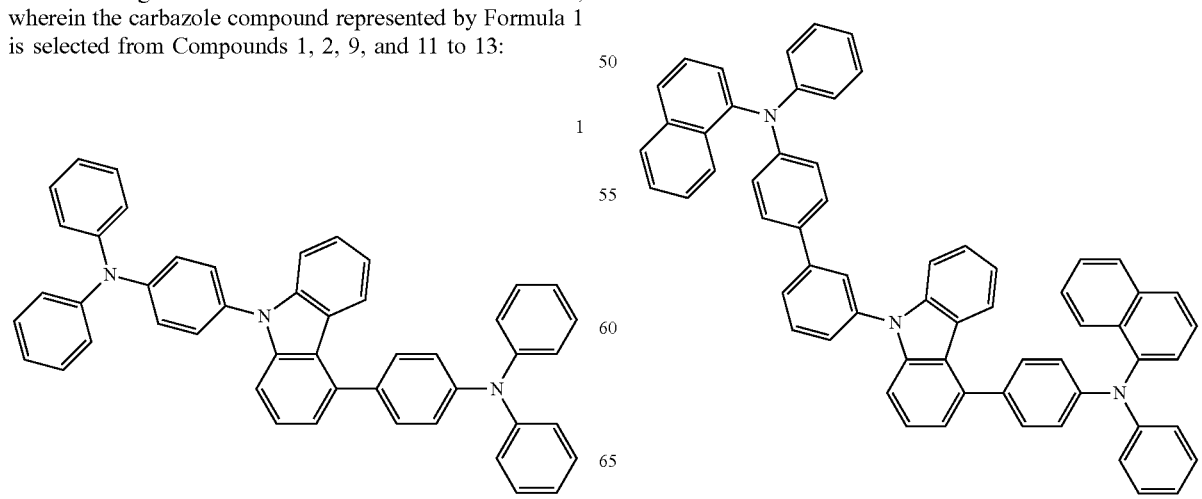

12
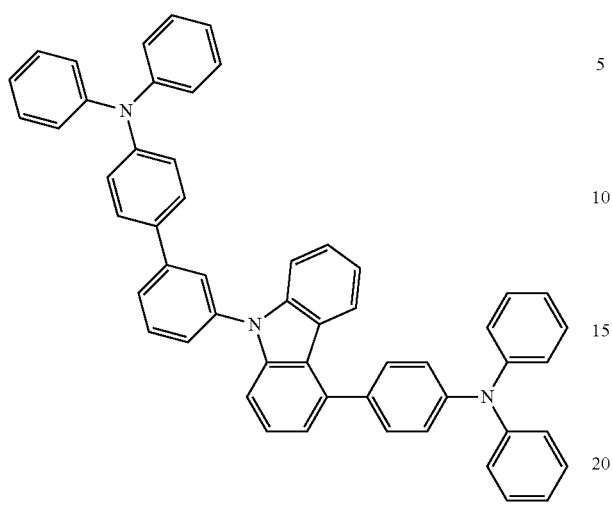
13
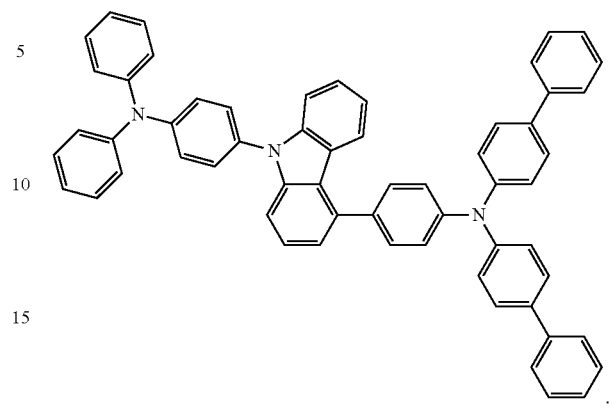
* * * * *